(12) United States Patent
Yoshida et al.

(10) Patent No.: US 9,259,202 B2
(45) Date of Patent: Feb. 16, 2016

(54) X-RAY DIAGNOSTIC APPARATUS

(71) Applicants: Kabushiki Kaisha Toshiba, Tokyo (JP);
Toshiba Medical Systems Corporation, Otawara-shi (JP)

(72) Inventors: Hajime Yoshida, Nasushiobara (JP);
Ryuji Zaiki, Utsunomiya (JP);
Masahiro Ozawa, Sakura (JP); Yusuke Narabu, Nasushiobara (JP); Masaki Kobayashi, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 395 days.

(21) Appl. No.: 13/859,275

(22) Filed: Apr. 9, 2013

(65) Prior Publication Data

US 2013/0266123 A1  Oct. 10, 2013

(30) Foreign Application Priority Data

Apr. 9, 2012 (JP) .................. 2012-088580
Mar. 12, 2013 (JP) .................. 2013-049393

(51) Int. Cl.
*A61B 6/00* (2006.01)
*A61B 6/12* (2006.01)

(52) U.S. Cl.
CPC . *A61B 6/545* (2013.01); *A61B 6/12* (2013.01);
*A61B 6/503* (2013.01); *A61B 6/504* (2013.01);
*A61B 6/4441* (2013.01)

(58) Field of Classification Search
CPC ...... A61B 6/4441; A61B 6/466; A61B 6/463;
A61B 6/547; A61B 6/102; A61B 6/503;
A61B 6/545; A61B 6/504; A61B 6/12
See application file for complete search history.

(56) References Cited

U.S. PATENT DOCUMENTS 8,463,014 B2  6/2013  Movassaghi et al.
2010/0014740 A1 *  1/2010  Movassaghi et al. ......... 382/132

FOREIGN PATENT DOCUMENTS

CN   101594824 A   12/2009
JP   2007-20891   2/2007

OTHER PUBLICATIONS

Translation of Chinese Office Action issued Oct. 10, 2014, in China Patent Application No. 201310118737.9.*
Translation of Applicant's arguments with the Amendment filed on Dec. 30, 2014, in China Patent Application No. 201310118737.9.*
Chinese Office Action issued Oct. 10, 2014, in China Patent Application No. 201310118737.9.

* cited by examiner

*Primary Examiner* — Glen Kao
(74) *Attorney, Agent, or Firm* — Oblon, McClelland, Maier & Neustadt, L.L.P.

(57) ABSTRACT

An X-ray diagnostic apparatus according to an embodiment includes a generating unit and a display controller. The generating unit generates a diagram illustrating the angle information of an arm. The display controller performs display control to visualize, together with the diagram generated by the generating unit, at least one of information showing the status of the arm when the arm is at an angle illustrated in the diagram and information showing the status of a subject to be imaged when the arm is at the angle illustrated in the diagram.

11 Claims, 18 Drawing Sheets

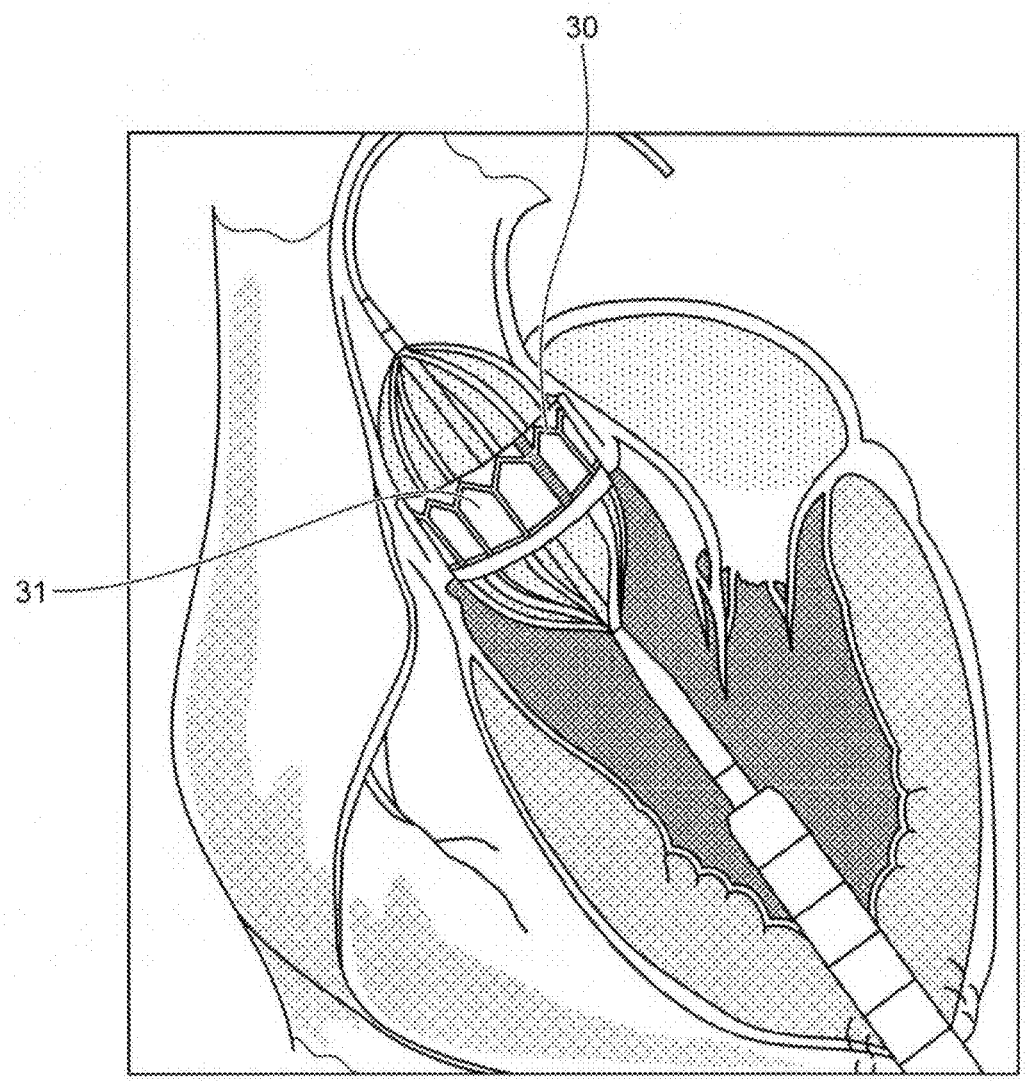

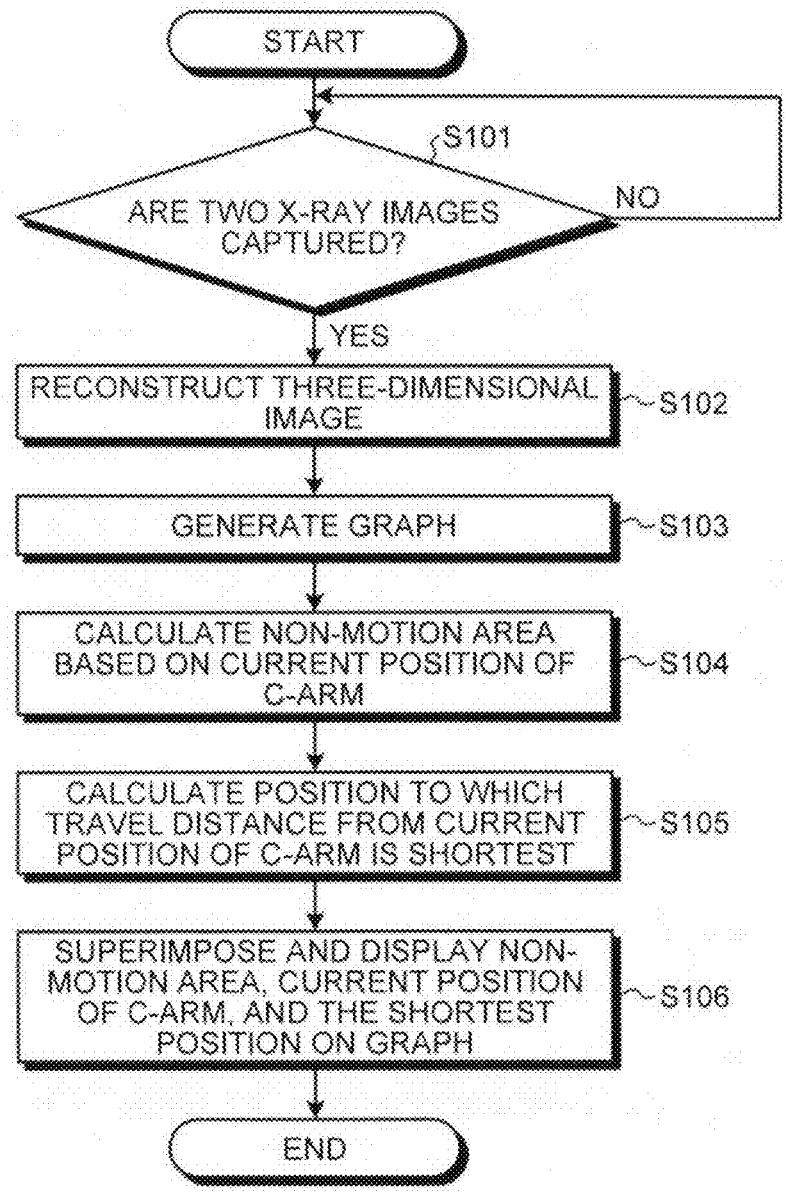

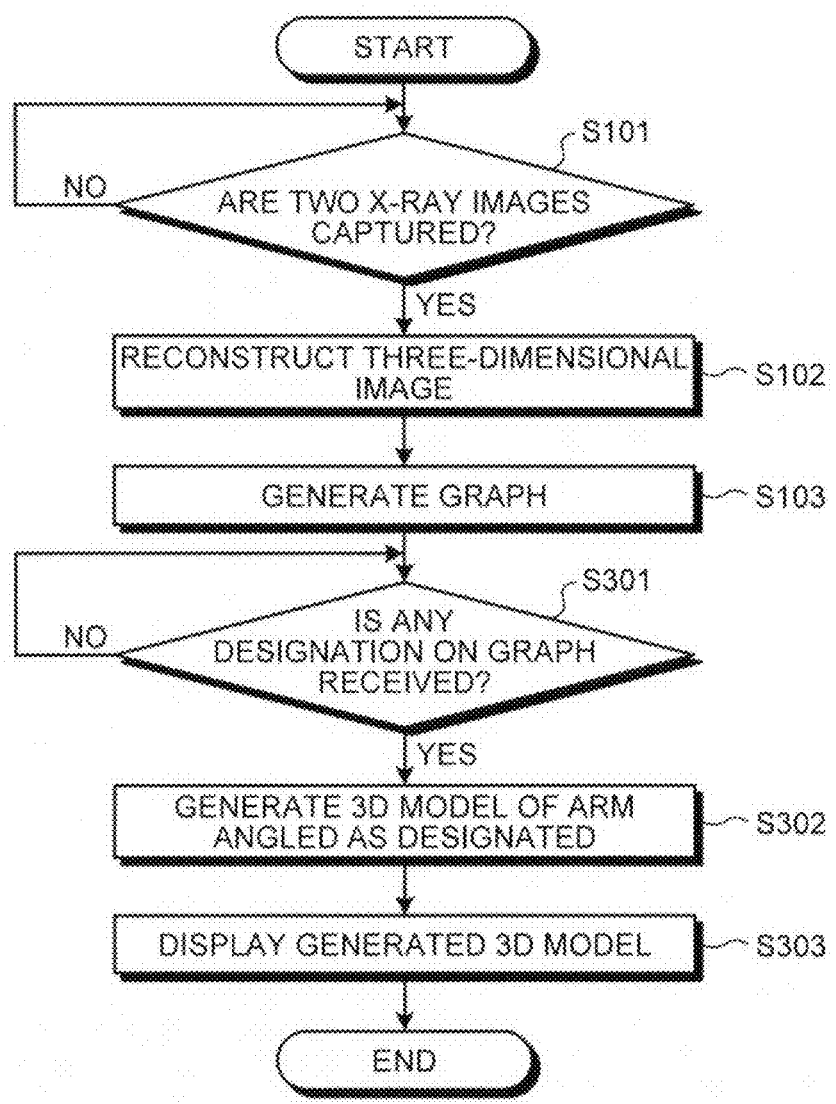

X-RAY DIAGNOSTIC APPARATUS

CROSS-REFERENCE TO RELATED APPLICATIONS

This application is based upon and claims the benefit of priority from Japanese Patent Application No. 2012-088580, filed on Apr. 9, 2012; and Japanese Patent Application No. 2013-049393, filed on Mar. 12, 2013, the entire contents of all of which are incorporated herein by reference.

FIELD

Embodiments described herein relate generally to an X-ray diagnostic apparatus.

BACKGROUND

In a treatment using an X-ray diagnostic apparatus, in particular, in transcatheter aortic valve replacement (TAVR), an optimal angle setting of an arm has been regarded as important for the observation of an aortic valve. For example, in TAVR, it is important to set the angle of the arm so that the aortic valve can be observed in the vertical direction (a direction in which the vertical cross section of the aortic valve is perpendicular to the image plane of an X-ray image) in order to implant an artificial valve in one dilation.

The cardiovascular angiographic analysis system aortic valve (CAAS A-Valve) by Pie Medical Imaging, LLC. is known as a clinical analysis application that provides the angle information of the arm for optimal observation in TAVR. The CAAS A-Valve reconstructs a three-dimensional image from two two-dimensional images of the origin of an aortic valve, and based on the reconstructed three-dimensional image, provides the angle information of an arm allowing the aortic valve to be observed in the vertical direction. The angle information of an arm provided by the CAAS A-Valve is informed to an X-ray diagnostic apparatus, thereby allowing the setting of the angle of the arm. In the above conventional technique, however, operability associated with the setting of the angle of the arm degrades in some cases.

BRIEF DESCRIPTION OF THE DRAWINGS

FIG. 3 is a schematic diagram illustrating an example of an X-ray image when TAVR according to the first embodiment is performed;

FIG. 9 is a flowchart illustrating the procedure of processing by the X-ray diagnostic apparatus according to the first embodiment;

FIG. 14 is flowchart illustrating the procedure of processing by an X-ray diagnostic apparatus according to the third embodiment;

DETAILED DESCRIPTION

First Embodiment

According to an embodiment, an X-ray diagnostic apparatus includes a generating unit and a display controller. The generating unit configured to generate a diagram illustrating the angle information of an arm. The display controller configured to perform display control to visualize, together with the diagram generated by the generating unit, at least one of information showing the status of the arm when the arm is at an angle illustrated in the diagram and information showing the status of a subject to be imaged when the arm is at the angle illustrated in the diagram.

Figure 1:
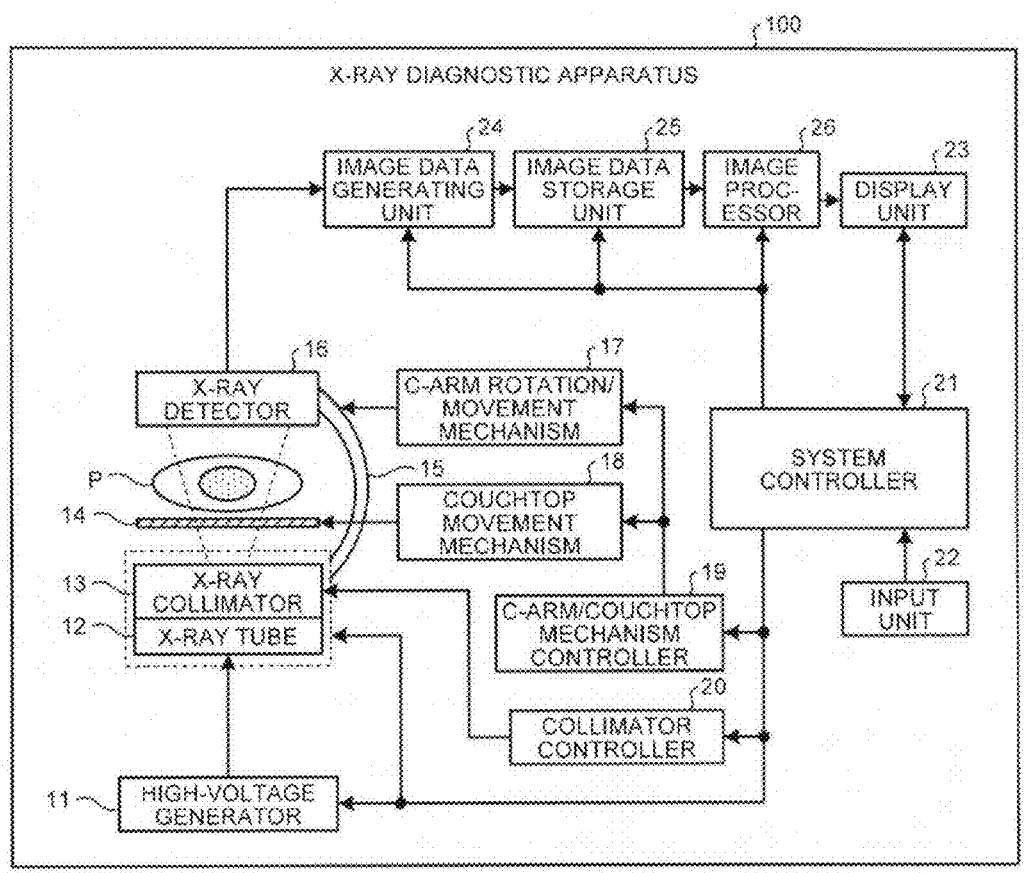
FIG. 1 is a diagram illustrating an example of the configuration of an X-ray diagnostic apparatus according to a first embodiment.

FIG. 1 is a diagram illustrating an example of the configuration of an X-ray diagnostic apparatus 100 according to a first embodiment. As illustrated in FIG. 1, the X-ray diagnostic apparatus 100 according to the first embodiment includes a high-voltage generator 11, an X-ray tube 12, an X-ray collimator 13, a couchtop 14, a C-arm 15, and an X-ray detector 16. The X-ray diagnostic apparatus 100 according to the first embodiment further includes a C-arm rotation/movement mechanism 17, a couchtop movement mechanism 18, a C-arm/couchtop mechanism controller 19, a collimator controller 20, a system controller 21, an input unit 22, and a display unit 23. The X-ray diagnostic apparatus 100 according to the first embodiment further includes an image data generating unit 24, an image data storage unit 25, and an image processor 26.

The high-voltage generator 11, under the control of the system controller 21, generates high voltage and supplies the generated high voltage to the X-ray tube 12. The X-ray tube 12 generates X-rays using the high voltage supplied from the high-voltage generator 11.

The X-ray collimator 13, under the control of the collimator controller 20, narrows down the X-rays generated by the X-ray tube 12 so that they are projected selectively onto an area of interest of a subject P. For example, the X-ray collimator 13 has four slidable collimator blades. The X-ray collimator 13, under the control of the collimator controller 20, slides these blades, thereby narrowing down the X-rays generated by the X-ray tube 12 and projecting them onto the subject P. The couchtop 14 is a bed on which the subject P is positioned, and is placed on a couch (not illustrated). The subject P is not included in the X-ray diagnostic apparatus 100.

The X-ray detector 16 detects the X-rays passing through the subject P. For example, the X-ray detector 16 has detecting elements arranged in a matrix manner. Each of the detecting elements converts the X-rays passing through the subject P into an electric signal and accumulates it, and transmits the accumulated electric signals to the image data generating unit 24. As an example, the X-ray detector 16 is made up of a flat panel detector (FPD) and the like.

The C-arm 15 holds the X-ray tube 12, the X-ray collimator 13, and the X-ray detector 16. The X-ray tube 12 and the X-ray collimator 13 are arranged with the C-arm 15 so that they face the X-ray detector 16 across the subject P.

The C-arm rotation/movement mechanism 17 is a mechanism for rotating and moving the C-arm 15, and the couchtop movement mechanism 18 is a mechanism for moving the couchtop 14. The C-arm/couchtop mechanism controller 19, under the control of the system controller 21, controls the C-arm rotation/movement mechanism 17 and the couchtop movement mechanism 18, thereby adjusting the rotation and movement of the C-arm 15 and the movement of the couchtop 14. The collimator controller 20, under the control of the system controller 21, adjusts the aperture of the collimator blades of the X-ray collimator 13 to control the projection range of the X-rays projected onto the subject P.

The image data generating unit 24 generates image data using the electric signals converted from the X-rays by the X-ray detector 16 and stores the generated image data in the image data storage unit 25. For example, the image data generating unit 24 performs current-to-voltage conversion, analog-to-digital conversion, and parallel-to-serial conversion on the electric signals received from the X-ray detector 16 to generate the image data.

The image data storage unit 25 stores therein the image data generated by the image data generating unit 24. For example, the image data storage unit 25 stores therein image data containing a radiograph of the aortic valve of the subject P.

The image processor 26 performs various types of image processing on the image data stored in the image data storage unit 25. The image processing by the image processor 26 will be described in detail later.

The input unit 22 receives various instructions from an operator, such as a doctor or a technician, who operates the X-ray diagnostic apparatus 100. For example, the input unit 22 includes a mouse, a keyboard, a button, a trackball, a joystick, or the like. The input unit 22 transfers instructions received from the operator to the system controller 21.

The display unit 23 displays a graphical user interface (GUI) for receiving instructions from the operator, the image data stored in the image data storage unit 25, and the like. For example, the display unit 23 includes a monitor. The display unit 23 may include a plurality of monitors.

The system controller 21 controls the operation of the entire X-ray diagnostic apparatus 100. For example, the system controller 21 controls the high-voltage generator 11 to adjust voltage supplied to the X-ray tube 12 in accordance with the instructions of the operator transferred from the input unit 22, thereby controlling a dose of X-rays projected onto the subject P or turning the X-rays on and off. For example, the system controller 21 controls the C-arm/couchtop mechanism controller 19 in accordance with the instructions of the operator, thereby controlling the rotation and movement of the C-arm 15 and the movement of the couchtop 14. For example, the system controller 21 controls the collimator controller 20 in accordance with the instructions of the operator to adjust the aperture of the collimator blades of the X-ray collimator 13, thereby controlling the projection range of the X-rays projected onto the subject P.

The system controller 21 controls image data generating processing performed by the image data generating unit 24, image processing performed by the image processor 26, analysis processing, or the like in accordance with the instructions of the operator. The system controller 21 controls the GUI for receiving the instructions of the operator, image data stored in the image data storage unit 25, and the like to be displayed on the monitor of the display unit 23.

Under the foregoing configuration, the X-ray diagnostic apparatus 100 according to the present embodiment improves arm operability in transcatheter aortic valve replacement (TAVR) through the processing by the image processor 26, which will be described in detail later. First, TAVR will be described. TAVR is a method of treatment in which a catheter is inserted from a femoral artery, a left ventricular apex, or the like, and an artificial valve is implanted into the main artery through the catheter. TAVR is receiving attention as a minimally invasive treatment for valvular disease such as aortic stenosis.

Figure 2A:
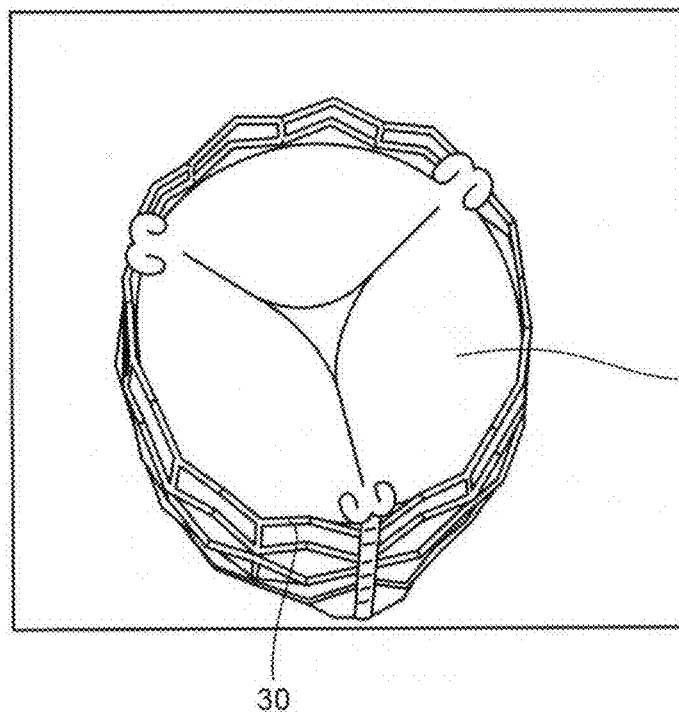
FIGS. 2A and 2B are diagrams illustrating an example of an artificial valve for use in TAVR according to the first embodiment.
Figure 2B:
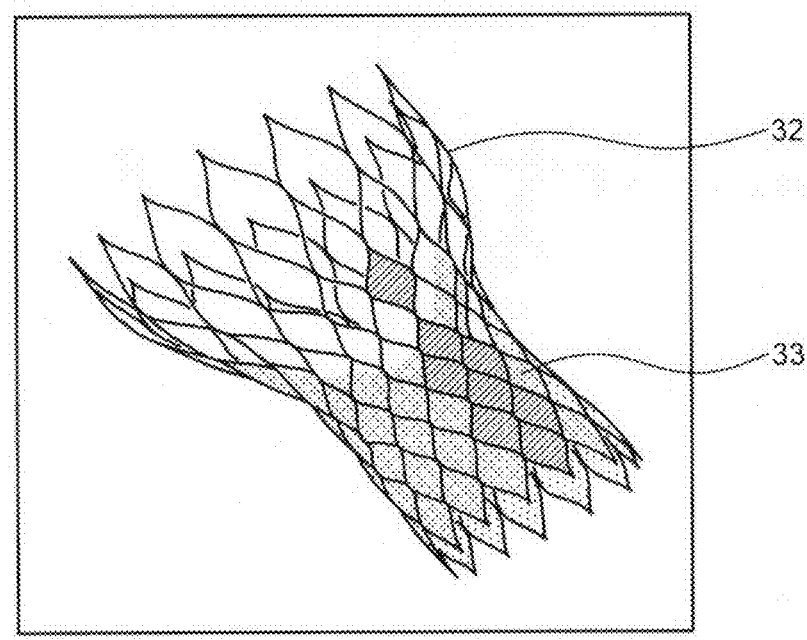

FIGS. 2A and 2B are diagrams illustrating an example of an artificial valve for use in TAVR according to the first embodiment. Specifically, FIG. 2A illustrates the Sapien of Edwards, and FIG. 2B illustrates the Corevalve of Medtronics, Inc. For example, an artificial valve for use in TAVR is, as illustrates in FIG. 2A, provided with three valves 31 inside a stent 30 and is implanted into a main artery through a catheter. For example, an artificial valve for use in TAVR, as illustrates in FIG. 2B, has a structure in which the outer diameter of a stent 32 having a valve 33 differs in position, allowing it to be stably implanted into a main artery.

Such an artificial valve is required to be implanted in nearly the same manner as the arrangement of the actual aortic valve in the main artery. To achieve this, a doctor performs TAVR while observing the aortic valve in the vertical direction (a direction in which the vertical cross section of the aortic valve is displayed on the display plane of an X-ray image). FIG. 3 is a schematic diagram illustrating an example of an X-ray image when TAVR according to the first embodiment is performed. FIG. 3 illustrates a case in which a catheter is inserted from the left ventricular apex to implant an artificial valve (the Sapien).

For example, as illustrated in FIG. 3, the doctor inserts the artificial valve having the stent 30 and the valves 31 through the catheter while observing the main artery in a direction in which the vertical cross section of the main artery, that is, the vertical cross section of the aortic valve is perpendicular to the display plane of an X-ray image. The doctor then implants the artificial valve at nearly the same position as the aortic valve, thereby allowing the angle and position of the valve 31 to be nearly the same as the angle and position of the aortic valve.

In order to observe the aortic valve in the above direction, in the conventional technique, the angle of the C-arm 15 is determined based on a graph illustrating the angle information of the C-arm 15 provided by the clinical analysis application, CAAS A-Valve. In other words, a doctor acquires, from the CAAS A-Valve, the angle of the C-arm 15 for imaging in a direction in which the vertical cross section of the aortic valve is perpendicular to the display plane and informs the X-ray diagnostic apparatus 100 of the acquired angle of the C-arm 15, thereby moving the C-arm 15 to a desired angle.

In the CAAS A-Valve, however, because the non-motion area of the C-arm 15 such as an area beyond the motion limit of the C-arm 15, the interference area between the C-arm 15 and a subject or couch, or the like, is not considered, a graph illustrating the angle information of the C-arm 15 is displayed for all angles. Thus, for example, it is difficult for an angle selected by the doctor on the graph to be reached owing to the position condition of the C-arm 15 in some cases. With the conventional technique, in such a case, it cannot be determined whether the angle is reachable until the angle is informed to the X-ray diagnostic apparatus 100. This degrades arm operability in TAVR.

Given this situation, the X-ray diagnostic apparatus 100 according to the present embodiment displays the non-motion area of the arm on a graph through the processing by the image processor 26 to allow the doctor to promptly determine whether the arm is reachable, thereby improving the arm operability. Hereinafter, the details of the image processor 26 according to the first embodiment will be described.

Figure 4:
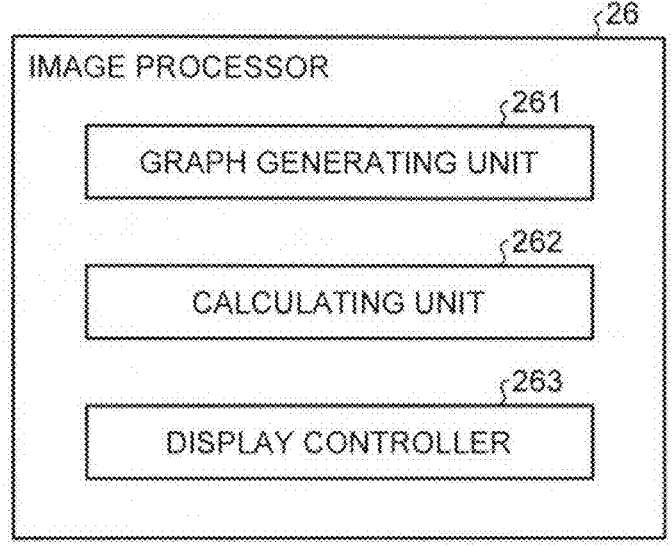
FIG. 4 is a diagram illustrating an example of the configuration of an image processor according to the first embodiment.

FIG. 4 is a diagram illustrating an example of the configuration of the image processor 26 according to the first embodiment. As illustrated in FIG. 4, the image processor 26 according to the first embodiment includes a graph generating unit 261, a calculating unit 262, and a display controller 263.

The graph generating unit 261 generates a diagram illustrating the angle information of the arm. Specifically, the graph generating unit 261 generates a graph illustrating the angle information of the arm with which the aortic valve is displayed at a particular angle with respect to the display plane of an X-ray image. For example, the graph generating unit 261 generates a graph illustrating the angle information of the arm with which the vertical cross section of the aortic valve is displayed at an angle nearly perpendicular or horizontal to the display plane of the X-ray image. The vertical cross section of the aortic valve here is a plane nearly perpendicular to the aortic valve when the aortic valve is closed. As an example of the graph, the graph generating unit 261 generates the optimal projection curve (Graph) with the CAAS A-Valve.

Figure 5A:
FIGS. 5A to 5C are diagrams illustrating an example of the generation of a three-dimensional image by a graph generating unit according to the first embodiment.
Figure 5B:
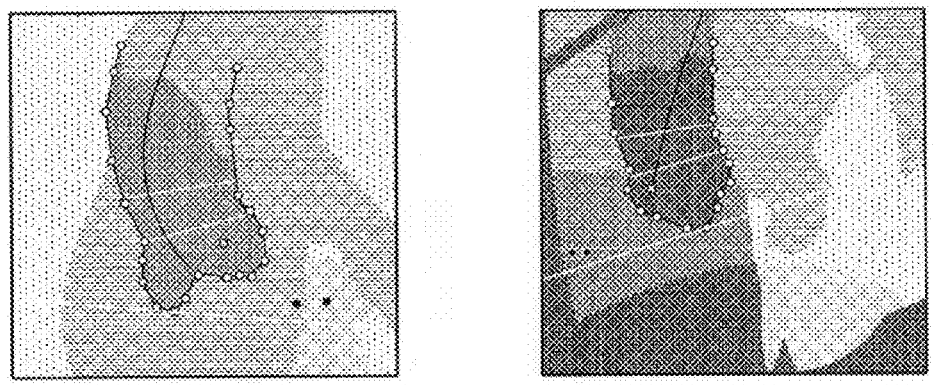
Figure 5C:
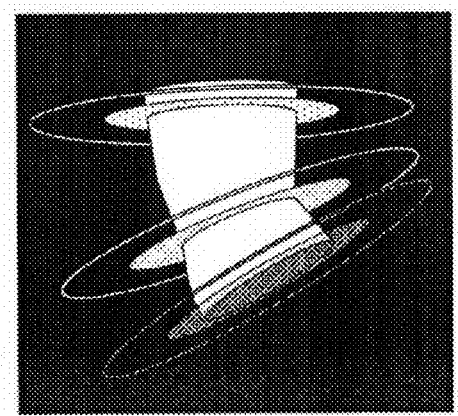

In other words, the graph generating unit 261 reconstructs a simple three-dimensional image from two two-dimensional images obtained by imaging the origin of the aortic valve in two directions, and based on the reconstructed three-dimensional image, generates a graph containing the optimal angle information of an arm for TAVR. FIGS. 5A to 5C are diagrams illustrating an example of the generation of a three-dimensional image by the graph generating unit 261 according to the first embodiment.

Prior to the processing by the graph generating unit 261, two two-dimensional images are captured. For example, with the aortic valve including the origin illustrated in FIG. 5A as a subject to be imaged, two two-dimensional images are radiographed as illustrated in FIG. 5B. The two two-dimensional images are captured so that the aortic valve is in the vertical direction in each of the images and that the images are spaced apart from each other making an angle, for example, of 45 degrees or more in terms of clinical angle.

As illustrated in FIG. 5B, the periphery of the aortic valve is traced in each of the two-dimensional images. Prior to the processing by the graph generating unit 261, the above capture of the two-dimensional images and tracing of the periphery of the aortic valve are performed by a doctor or an engineer. Based on two two-dimensional images after the above processing and auxiliary information such as the form of blood vessels (for example, a cylinder) and the like, the graph generating unit 261 generates a simple three-dimensional image, for example, as illustrated in FIG. 5C. The graph generating unit 261 reconstructs the three-dimensional image while complementing data from the two two-dimensional images and the auxiliary information.

The graph generating unit 261 informs the display controller 263, which will be described later, to display the reconstructed three-dimensional image at the display unit 23 as illustrated in FIG. 5C. The doctor or the engineer designates, through the input unit 22, the position of the aortic valve on the three-dimensional image displayed at the display unit 23 under the control of the display controller 263. Specifically, as illustrated in FIG. 5C, the doctor or the engineer moves a plane within the range from the upper end to the lower end of the three-dimensional image of the aortic valve, thereby designating a particular position as the position of the aortic valve.

Upon the designation of the position of the aortic valve by the doctor or the engineer, the graph generating unit 261 generates a graph illustrating the angle information of the arm in which the designated position of the plane is observed in the vertical direction. In other words, the graph generating unit 261 generates a graph illustrating the angle information of the arm in which the aortic valve is observed in the vertical direction.

Figure 6:
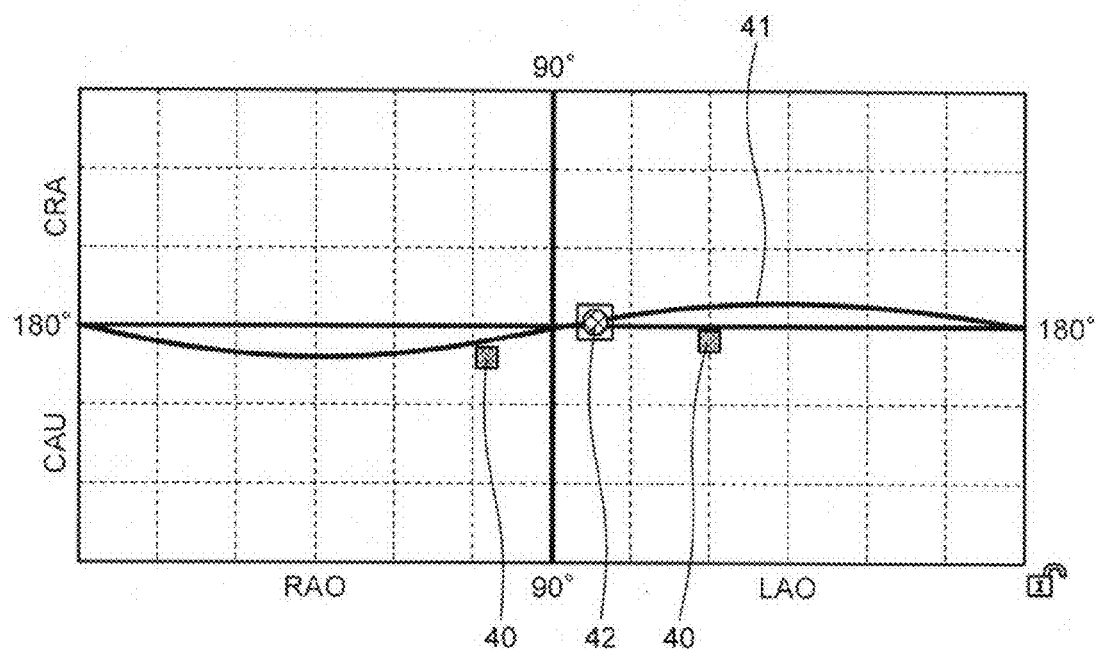
FIG. 6 is a diagram illustrating an example of a graph generated by the graph generating unit according to the first embodiment.

FIG. 6 is a diagram illustrating an example of a graph generated by the graph generating unit 261 according to the first embodiment. In FIG. 6, the longitudinal axis denotes clinical angles in cranial direction (CRA) and caudal direction (CAU), and the horizontal axis denotes clinical angles of right anterior oblique (RAO) and left anterior oblique (LAO).

For example, as illustrated in FIG. 6, the graph generating unit 261 generates a graph illustrating points 40 indicating the angles of the C-arm at which the two two-dimensional images are captured, a curve 41 that is the optimal projection curve, and a point 42 indicating a recommended angle. The optimal projection curve is a curve representing the angle of the C-arm 15 at which an image of the aortic valve is captured in the vertical direction. In other words, it means that when the angle of the C-arm 15 is set to be any angle on the curve 41, an X-ray image in which the aortic valve is observed in the vertical direction is captured.

The recommended angle means the recommended angle of the C-arm calculated through predetermined calculation. With the conventional technique, it cannot always be determined whether the recommended angle is within the motion area of the C-arm 15 or what position is within the motion area of the C-arm 15. Given this situation, in order to promptly perform such determination, the image processor 26 of the present embodiment calculates the non-motion area of the C-arm 15 as described later.

Returning back to FIG. 4, based on the current position information of the C-arm 15, the calculating unit 262 calculates the interference area between the C-arm 15 and the subject or the couch as information showing the status of the C-arm 15. Specifically, the calculating unit 262 acquires the current position of the C-arm 15 and an area in which the C-arm 15 interferes with the couch and the subject from the system controller 21. The calculating unit 262 then calculates the interference area where interference with the couch and the subject occurs at the current position of the C-arm 15 as a non-motion area. The calculating unit 262 acquires an area beyond the motion limit of the arm as the non-motion area of the arm from the system controller 21. Specifically, the calculating unit 262 acquires the stroke limits of all motion axes of the C-arm 15 from the system controller 21, thereby calculating an area that cannot be positioned owing to the stroke limits as the non-motion area. The stroke limits of all motion axes of the C-arm 15 are determined when the X-ray diagnostic apparatus 100 is installed.

Figure 7:
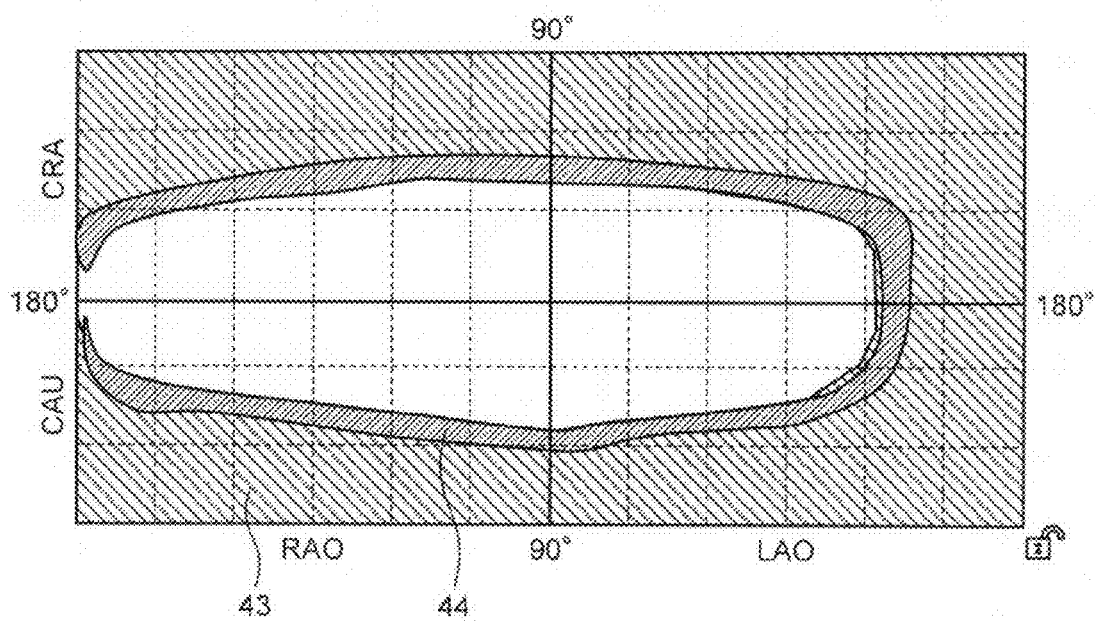
FIG. 7 is a diagram illustrating an example of the non-motion area of a C-arm calculated by a calculating unit according to the first embodiment.

FIG. 7 is a diagram illustrating an example of the non-motion area of the C-arm 15 calculated by the calculating unit 262 according to the first embodiment. For example, as illustrated in FIG. 7, the calculating unit 262 calculates non-motion areas of the C-arm 15 in the graph of the clinical angles illustrated in FIG. 6. As an example, as illustrated in FIG. 7, the calculating unit 262 calculates an area 43 as an area in which positioning is impossible owing to the stroke limits and an interference area 44 where interference with the couch and the subject occurs at the current position of the C-arm 15.

Returning back to FIG. 4, the display controller 263 performs display control to visualize, together with the diagrams generated by the graph generating unit 261, at least one of information showing the status of the C-arm 15 when the C-arm 15 is at an angle illustrated in the diagrams and information showing the status of a subject to be imaged when the C-arm 15 is at the angle illustrated in the diagrams. Specifically, the display controller 263 allows, together with the graph, at least one of the motion area of the C-arm 15, an area beyond the motion area of the C-arm 15, and the interference area, as information showing the status of the C-arm 15, to be displayed. The following describes an example of displaying information showing the status of the C-arm 15. Information showing the status of a subject to be imaged will be described in detail later.

For example, the display controller 263 allows the display unit 23 to display a display graph illustrating the non-motion area of the C-arm 15 on the graph generated by the graph generating unit 261. Specifically, the display controller 263 allows the display unit 23 to display a display graph in which the area that is unable to be positioned owing to the stroke limits and is calculated by the calculating unit 262 and the interference area are superimposed on the graph. In other words, the display controller 263 informs the system controller 21 to allow the display unit 23 to display the display graph on which the area that is unable to be positioned owing to the stroke limits and the interference area are superimposed.

Figure 8A:
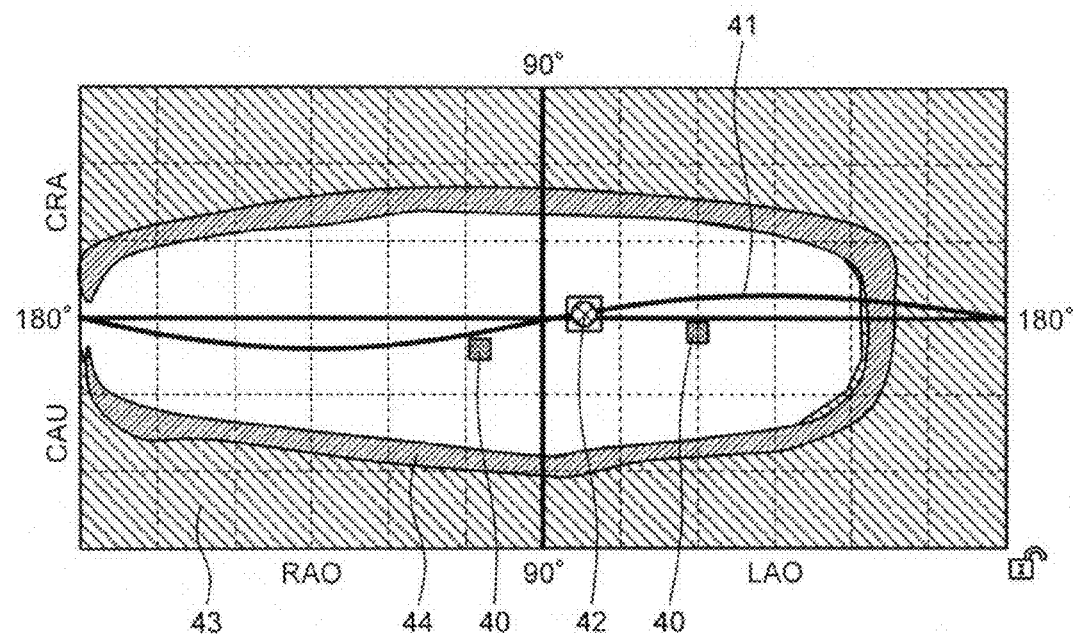
FIGS. 8A and 8B are diagrams illustrating an example of display control by a display controller according to the first embodiment.
Figure 8B:
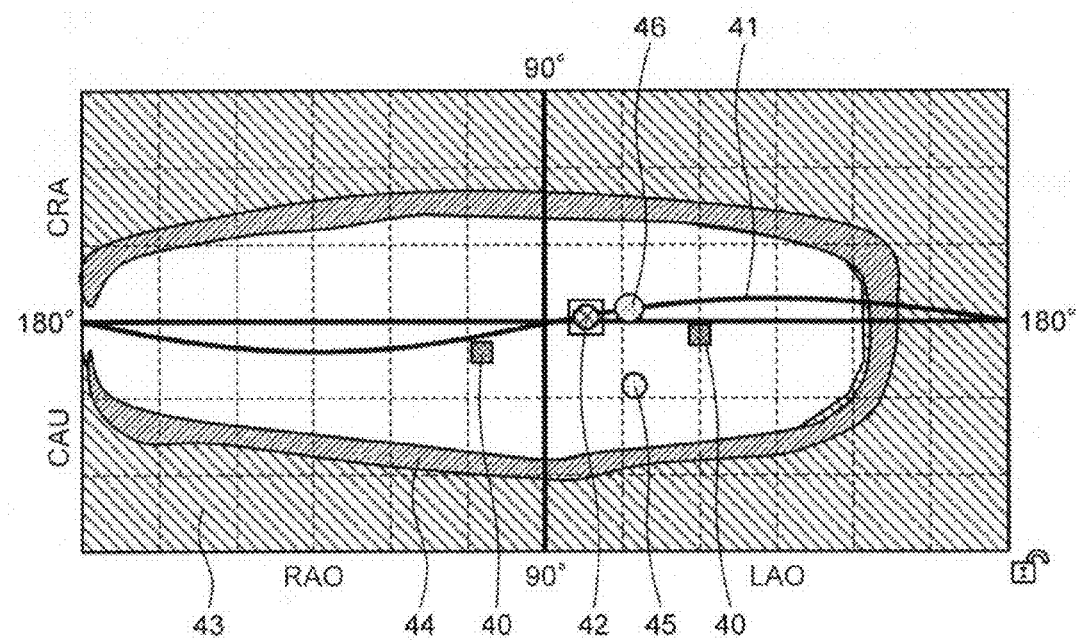

FIGS. 8A and 8B are diagrams illustrating an example of display control by the display controller 263 according to the first embodiment. For example, as illustrated in FIG. 8A, the display controller 263 according to the first embodiment allows the display unit 23 to display a display graph in which the non-motion area of the C-arm 15 calculated by the calculating unit 262 is superimposed on the graph generated by the graph generating unit 261. The doctor or the engineer can thereby determine at a glance whether the point 42 indicating the recommended angle is in the motion area or the non-motion area. The doctor or the engineer can also recognize at a glance which area is a non-motion area. As a result, the X-ray diagnostic apparatus 100 according to the first embodiment can determine the angle of the C-arm 15 easily, improving the operability of the C-arm 15 in TAVR.

The display controller 263 allows the display unit 23 to display a display graph illustrating the current position of the arm and a position whose distance from the current position is shortest with its angle being one of the angles of the arm at which the aortic valve is displayed at a particular angle with respect to the display plane of an X-ray image. For example, as illustrated in FIG. 8B, the display controller 263 superimposes and displays, in addition to the non-motion area of the C-arm 15, a current angle 45 of the C-arm 15 and an angle 46 to which travel distance from the current angle 45 is shortest among the angles of the C-arm 15 which allows observation of the aortic valve in the vertical direction, on the graph. In such a case, the display controller 263 calculates as the angle 46 an angle to which distance from the current angle 45 of the C-arm is shortest among the angles on the curve 41 and superimposes and displays it on the graph.

This minimizes the travel distance of the C-arm 15 to observe the aortic valve in the vertical direction, thereby preventing the movement of the C-arm 15 from hindering an operation in TAVR. For example, in TAVR, in addition to a doctor who implants an artificial valve, some anesthesiologists, supporting doctors, nurses, engineers, and the like are present in an operating room, in which some monitors, heart-lung machines, surgical instruments, and the like are placed. In such an environment, it is desired to minimize the movement of the C-arm. As described above, the X-ray diagnostic apparatus 100 according to the first embodiment minimizes the travel distance of the C-arm 15 to observe the aortic valve in the vertical direction, thereby fulfilling the demand.

Next, processing by the X-ray diagnostic apparatus 100 according to the first embodiment will be described using FIG. 9. FIG. 9 is a flowchart illustrating the procedure of the processing by the X-ray diagnostic apparatus 100 according to the first embodiment. As illustrated in FIG. 9, in the X-ray diagnostic apparatus 100 according to the first embodiment, when two X-ray images for TAVR is captured (Yes at S101), the graph generating unit 261 reconstructs a three-dimensional image based on the periphery of a main artery traced on each of the two X-ray images and auxiliary information (S102).

Based on the position of an aortic valve designated on the generated three-dimensional image, the graph generating unit 261 generates a graph illustrating the angle information of the C-arm 15 to observe the aortic valve in the vertical direction (S103). The calculating unit 262 calculates a non-motion area based on the current position of the C-arm 15 (S104).

The display controller 263 calculates a position to which travel distance from the current position of the C-arm 15 is shortest (S105). The display controller 263 then superimposes and displays the non-motion area, the current position of the C-arm 15, and the shortest position, on the graph generated by the graph generating unit 261 (S106). Until the two X-ray images are captured, the X-ray diagnostic apparatus 100 is on standby (No at S101).

As described above, in the first embodiment, the graph generating unit 261 generates a diagram illustrating the angle information of the arm. The display controller 263 performs display control to visualize, together with the diagram generated by the graph generating unit 261, at least one of information showing the status of the arm when the arm is at an angle illustrated in the diagram and information showing the status of a subject to be imaged when the arm is at the angle illustrated in the diagram. The X-ray diagnostic apparatus 100 according to the first embodiment can determine the angle of the C-arm 15 easily by knowing in advance a range within which the arm can be positioned, thereby improving the operability of the C-arm 15 in TAVR.

In the first embodiment, based on the current position information of the arm, the calculating unit 262 calculates the interference area between the arm and the subject P or the couch as information showing the status of the arm. The graph generating unit 261 generates a graph as information showing angle information. The display controller 263 allows, together with the graph, at least one of the motion area of the arm, an area beyond the motion area of the arm, and the interference area to be displayed as information showing the status of the C-arm 15. The X-ray diagnostic apparatus 100 according to the first embodiment can thus display a non-motion area with the current position of the arm taken into consideration, thereby allowing more accurate display of an angle of the arm at which the arm is unable to be positioned.

The X-ray diagnostic apparatus 100 according to the first embodiment allows a non-motion area owing to stroke limits and a non-motion area with interference at the current position of the C-arm 15 taken into account to be displayed for a doctor or an engineer, thereby allowing the angle of the C-arm 15 to be determined easily.

In the first embodiment, the graph generating unit 261 generates a graph illustrating the angle information of the arm with which the vertical cross section of the aortic valve is displayed at an angle nearly perpendicular or horizontal to the display plane of an X-ray image. The X-ray diagnostic apparatus 100 according to the first embodiment can thus provide the optimal angle of the arm for TAVR.

In the first embodiment, the vertical cross section is a plane nearly perpendicular to the aortic valve when the aortic valve is closed. The X-ray diagnostic apparatus 100 according to the first embodiment can thus align the status of the actual aortic valve with the status of an artificial valve accurately.

In the first embodiment, the display controller 263 allows the display unit 23 to display a display graph illustrating the current position of the C-arm 15 and a position whose distance from the current position of the arm is shortest out of the distances with the angles of the arm at which the aortic valve is displayed with a particular angle with respect to the display plane of the X-ray image. The X-ray diagnostic apparatus 100 according to the first embodiment can thus move the C-arm 15 to the optimal angle with a minimum movement, thereby preventing a hindrance during an operation.

Second Embodiment

The above first embodiment describes a case in which a non-motion area, the current position of the C-arm 15, and a position to which travel distance of the C-arm 15 is shortest are superimposed and displayed on a graph. The second embodiment will describe a case in which the C-arm 15 is moved through an operation on the graph.

Figure 10:
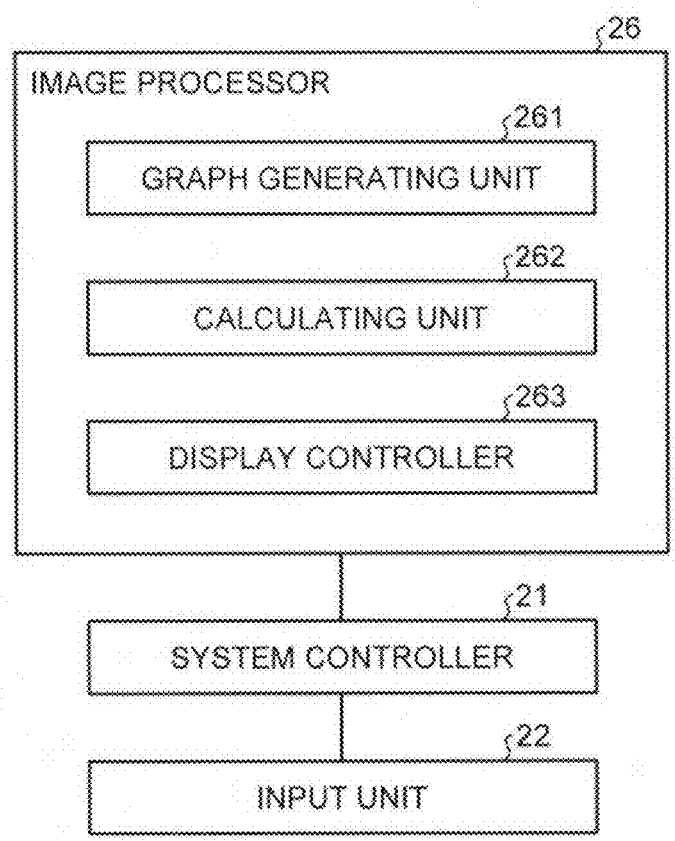
FIG. 10 illustrates an example of the configuration of an image processor, a system controller, and an input unit according to a second embodiment.

FIG. 10 illustrates an example of the configuration of the image processor 26, the system controller 21, and the input unit 22 according to the second embodiment. The X-ray diagnostic apparatus 100 according to the second embodiment is different from the first embodiment in receiving processing by the input unit 22 and control by the system controller 21. Hereinafter, these matters will be mainly described.

Figure 11:
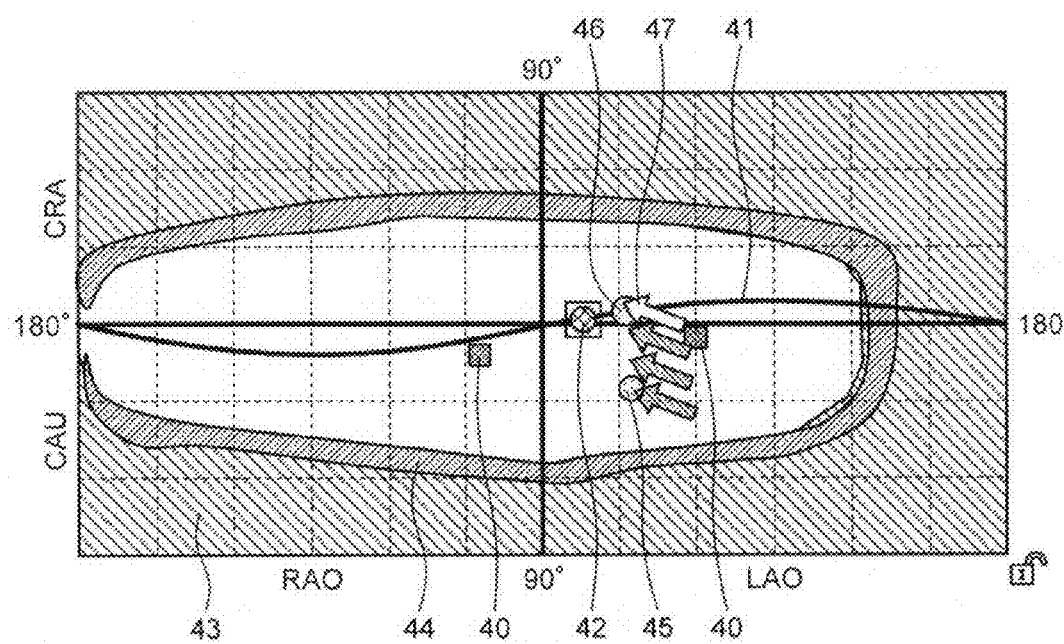
FIG. 11 is a diagram for illustrating receiving processing by the input unit according to the second embodiment.

The input unit 22 according to the second embodiment receives an input operation onto a display graph displayed on the display unit 23 by the display controller 263. Specifically, the input unit 22 receives a movement operation on the current position of the C-arm 15 illustrated on the display graph displayed by the display unit 23. FIG. 11 is a diagram for illustrating receiving processing by the input unit 22 according to the second embodiment.

For example, as illustrated by a arrow 47 in FIG. 11, the input unit 22 receives an input operation of dragging the current angle 45 of the C-arm 15 to the angle 46 to which travel distance is shortest by a doctor or an engineer with a mouse. The input unit 22 informs the system controller 21 of the information on the received input operation. In other words, the input unit 22 informs the system controller 21 of information on the angle 46 of the C-arm 15 as the destination of the movement.

The system controller 21 moves the C-arm 15 in accordance with the input operation received by the input unit 22. Specifically, the system controller 21 informs the C-arm/couchtop mechanism controller 19 of the information of the C-arm 15 angle after the input operation informed from the input unit 22, and moves the C-arm 15 to the angle after the input operation. For example, the system controller 21 informs the C-arm/couchtop mechanism controller 19 of the information on the angle 46 of the C-arm 15 as the destination of the movement and moves the C-arm 15 to the position with the angle 46.

Figure 12:
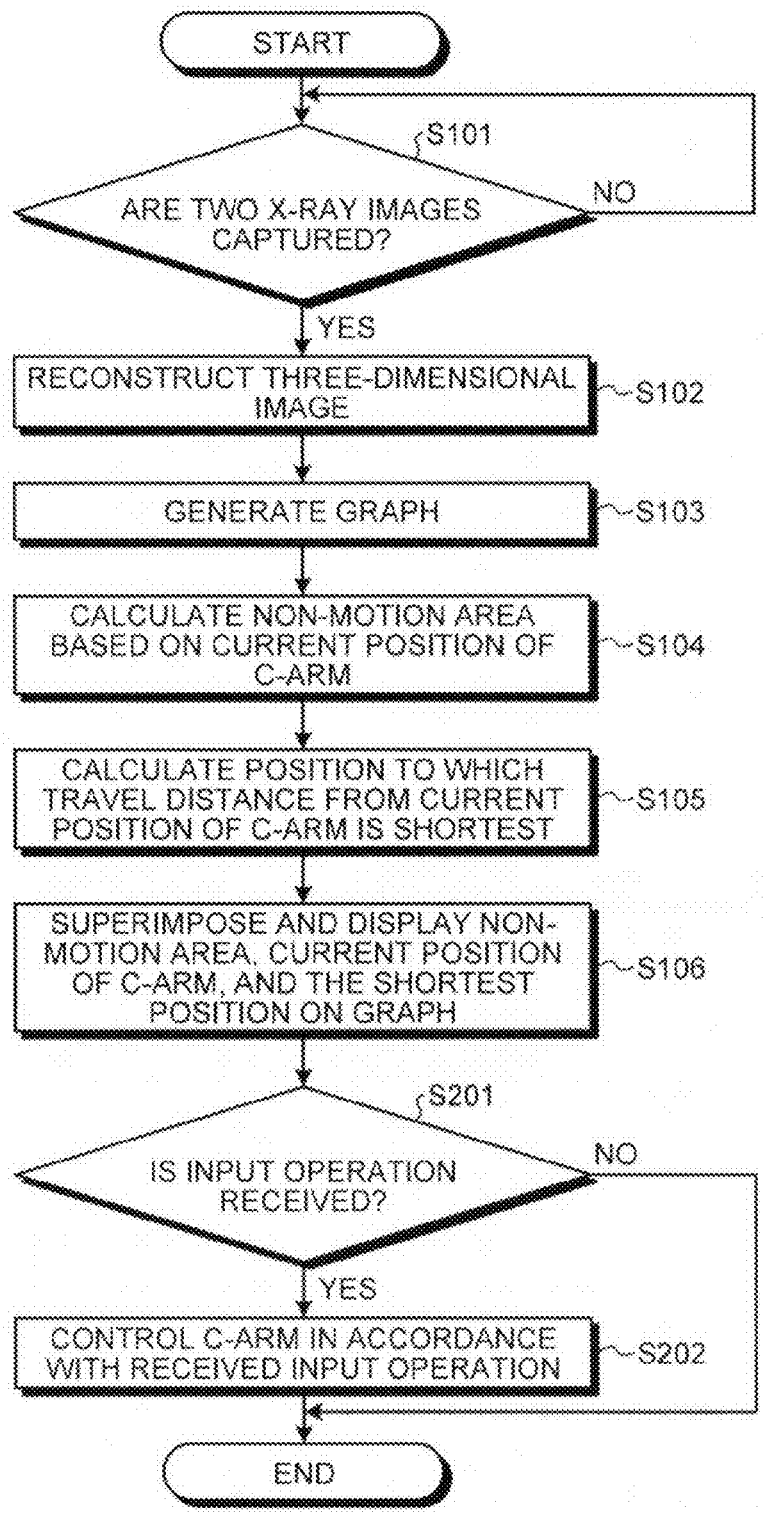
FIG. 12 is a flowchart illustrating the procedure of processing by an X-ray diagnostic apparatus according to the second embodiment.

Next, processing by the X-ray diagnostic apparatus 100 according to the second embodiment will be described using FIG. 12. FIG. 12 is a flowchart illustrating the procedure of the processing by the X-ray diagnostic apparatus 100 according to the second embodiment. In FIG. 12, like processing as in the procedure of the processing by the X-ray diagnostic apparatus 100 according to the first embodiment illustrated in FIG. 9 will be referred to by like step numbers, and the description of the details thereof will be omitted.

As illustrated in FIG. 12, in the X-ray diagnostic apparatus 100 according to the second embodiment, when two X-ray images for TAVR are captured (Yes at S101), the graph generating unit 261 reconstructs a three-dimensional image (S102) and generates a graph (S103). The calculating unit 262 then calculates a non-motion area based on the current position of the C-arm 15 (S104).

The display controller 263 calculates a position to which travel distance is shortest (S105) and superimposes and displays the non-motion area, the current position of the C-arm, and the shortest position on the graph (S106).

When the input unit 22 receives an input operation through the graph displayed on the display unit 23 (Yes at S201), it informs the system controller 21 of the information on the received input operation. The system controller 21 then controls the C-arm/couchtop mechanism controller 19 in accordance with the input operation received by the input unit 22, thereby controlling the C-arm 15 (S202). Until the two X-ray images are captured, the X-ray diagnostic apparatus 100 is on standby (No at S101).

As described above, in the second embodiment, the input unit 22 receives an input operation onto a display graph displayed on the display unit 23 under the control of the display controller 263. The system controller 21 moves the C-arm 15 in accordance with the input operation received by the input unit 22. The X-ray diagnostic apparatus 100 according to the second embodiment can thus determine a position of the C-arm 15 on the graph and moves the C-arm 15 to the position, thereby further improving the operability of the arm in TAVR.

Third Embodiment

The above first and second embodiments describe cases in which at least one of the motion area of the arm, an area beyond the motion limit of the arm, and the interference area are displayed as information showing the status of the arm. The third embodiment will describe a case in which an outside view illustrating the position relation between the arm and a subject or a couch is displayed as information showing the status of the arm. The third embodiment is different from the first and second embodiments in the contents displayed by the display controller 263. Hereinafter, this matter will be mainly described.

The display controller 263 according to the third embodiment allows, together with a graph, an outside view illustrating the position relation of the arm with a subject or a couch to be displayed as information showing the status of the arm. Specifically, when the C-arm 15 is angled at a certain angle, the display controller 263 displays an outside view illustrating the position relation between the C-arm 15 and the subject or between the C-arm 15 and the couch, together with a graph.

Figure 13:
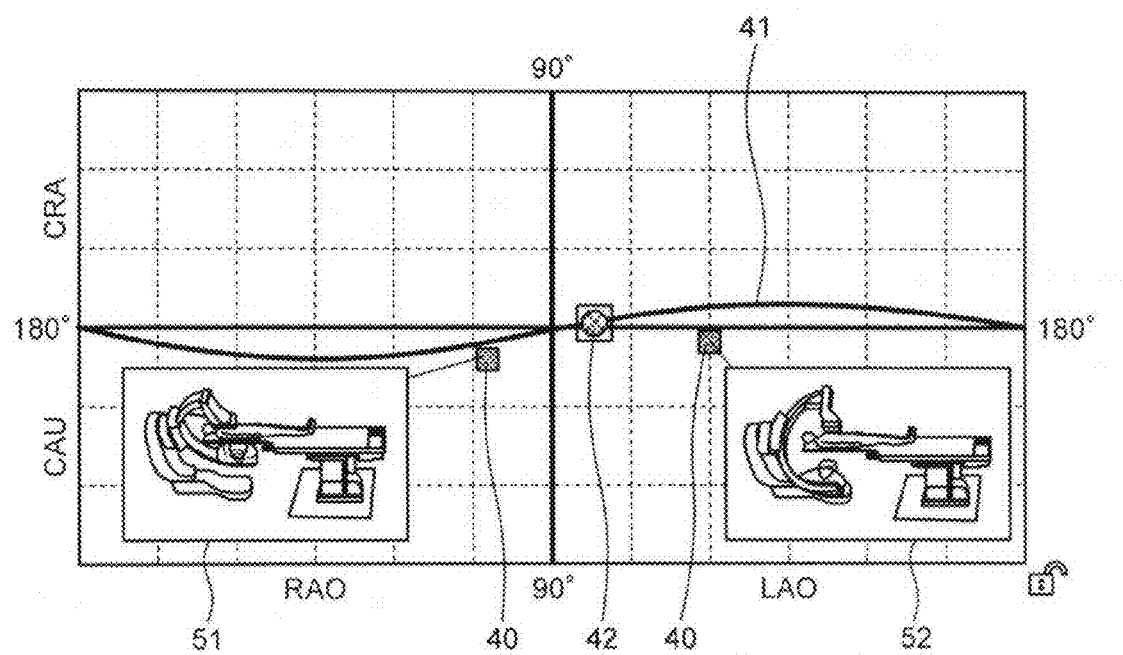
FIG. 13 is a diagram illustrating an example of display control by a display controller according to a third embodiment.

FIG. 13 is a diagram illustrating an example of display control by the display controller according to the third embodiment. For example, as illustrated in FIG. 13, the display controller 263 according to the third embodiment allows the display unit 23 to display a display graph in which a 3D model with the C-arm angled at a particular angle is superimposed on the graph generated by the graph generating unit 261. As an example, as illustrated in FIG. 13, the display controller 263 allows the display unit 23 to display a display graph in which a 3D model 51 with the C-arm 15 angled at an angle corresponding to the left-hand point 40 of the two points 40 representing the angles of the C-arm at which two two-dimensional images are captured, and a 3D model 52 with the C-arm 15 angled at an angle corresponding to the right-hand point 40 of the two points 40 are superimposed on the graph.

In other words, the display controller 263 allows the 3D model generated by the image processor 26 to be superimposed on the graph generated by the graph generating unit 261 and to be displayed on the display unit 23. The 3D model generated by the image processor 26 may be a projection image with the angle of the C-arm 15 angled at a designated angle generated from the three-dimensional data of the apparatus stored in advance or may be read from three-dimensional images with the C-arm 15 angled at respective angles stored in advance.

In one example, when an operator designates a point (angle) on the graph, the image processor 26 reads the three-dimensional data of the apparatus, angles the C-arm 15 in the read three-dimensional data at the designated angle, and generates a 3D model by projection processing from a viewpoint position facilitating observation. In another example, when the operator designates a point (angle), the image processor 26 reads a three-dimensional image in which the C-arm 15 is angled at the designated angle. The three-dimensional data of the apparatus and the three-dimensional images for respective angles are stored in, for example, the image data storage unit 25.

As illustrated in FIG. 13, the 3D model generated by the image processor 26 is a three-dimensional image that allows understanding of the position relation between the subject and the C-arm 15, the position relation between the couch and the C-arm 15, or the like. This allows the operator such as a doctor or an engineer to intuitively understand the state of the apparatus when the C-arm 15 is angled at a certain angle. The subject illustrated in FIG. 13 is allowed, for example, through the input unit 22, to change its size. Specifically, the displayed size of the subject on the couch can be changed to an optional size in accordance with the current physical constitution of the subject. The example illustrated in FIG. 13 is an example, and the display controller 263 allows a 3D model corresponding to a point on the graph designated by the operator, to be displayed.

The display controller 263 allows display of a 3D model that illustrates, in addition to the position relations between the C-arm 15 and the subject and between the C-arm 15 and the couch, the relation with peripheral equipment and an operator. In other words, the display controller 263 allows the outside view to further display the position relation with at least either the peripheral equipment or the operator as information showing the status of the arm. For example, when a hybrid operation in which an intravascular treatment using a catheter and a surgical procedure are simultaneously performed is performed, various instruments are placed around the couch and staff of various types stand thereby.

Given this situation, in the X-ray diagnostic apparatus 100 according to the third embodiment, the image data storage unit 25 stores therein in advance information on the arrangement of the peripheral equipment, the standing position of the operator, and the like with respect to the apparatus, and the information can be displayed simultaneously. For example, when generating a projection image from the three-dimensional data of the apparatus, the image processor 26 arranges information showing the peripheral equipment and the operator and then performs projection processing to generate a 3D model. This allows the 3D model displayed by the display controller 263 to represent the position relation between the C-arm 15 and the peripheral equipment, the position relation between the C-arm 15 and the operator, and the like.

The position relation with the peripheral equipment or the operator may be acquired by analyzing images collected by a camera. For example, with a plurality of cameras installed around the apparatus, the image processor 26 may generate a 3D model by analyzing the position relations between the apparatus and the peripheral equipment and between the apparatus and the operator using images collected by the cameras.

The position relation with the peripheral equipment and the operator may be switched, for example, for each inspection protocol. For example, for an inspection involving a few pieces of peripheral equipment, the display controller 263 allows 3D models each representing the position relation of the C-arm 15 with the subject, the couch, or the operator, to be displayed. For example, for an inspection involving a few pieces of peripheral equipment, the display controller 263 allows 3D models each representing the position relation of the C-arm 15 with the subject, the couch, the peripheral equipment, or the operator, to be displayed. Approximate arrangement positions may be registered in advance for each inspection protocol. Thereby, for example, the X-ray diagnostic apparatus 100 can appropriately recognize the positions of objects and persons, even when the positions of the peripheral equipment and the standing position of the operator change depending on inspections.

Next, processing by the X-ray diagnostic apparatus 100 according to the third embodiment will be described using FIG. 14. FIG. 14 is a flowchart illustrating the procedure of the processing by the X-ray diagnostic apparatus 100 according to the third embodiment. In FIG. 14, like processing as in the procedure of the processing by the X-ray diagnostic apparatus 100 according to the first embodiment illustrated in FIG. 9 will be referred to by like step numbers, and the description of the details thereof will be omitted.

As illustrated in FIG. 14, in the X-ray diagnostic apparatus 100 according to the third embodiment, when two X-ray images for TAVR are captured (Yes at S101), the graph generating unit 261 reconstructs a three-dimensional image (S102) and generates a graph (S103). The image processor 26 then determines whether designation on the graph is received (S301).

When designation on the graph is received (Yes at S301), the image processor 26 generates a 3D model of the arm angled at the designated angle (S302). The display controller 263 allows the display unit 23 to display a display graph in which the generated 3D model is superimposed on the graph (S303). Until the two X-ray images are captured, the X-ray diagnostic apparatus 100 is on standby (No at S101). Until designation on the graph is received, the X-ray diagnostic apparatus 100 is on standby (No at S301).

As described above, in the third embodiment, the graph generating unit 261 generates a graph as information showing angle information. The display controller 263 allows, together with the graph, an outside view illustrating the position relation of the arm with the subject or the couch to be displayed as information showing the status of the arm. The X-ray diagnostic apparatus 100 according to the third embodiment thus allows an operator to know what layout the apparatus takes when the C-arm 15 is angled.

In the third embodiment, the display controller 263 allows the outside view to further display the position relation with at least either the peripheral equipment or the operator as information showing the status of the arm. The X-ray diagnostic apparatus 100 according to the third embodiment thus allows the operator to know at what positions the apparatus, the operator, and the peripheral equipment are arranged when the C-arm is angled.

In the third embodiment, the outside view illustrating the position relations of the arm with the subject, the couch, the peripheral equipment, and the operator is generated by analyzing images collected by cameras. The X-ray diagnostic apparatus 100 according to the third embodiment can thus automatically recognize a change in the arrangement of the peripheral equipment and the standing positions of persons and respond accordingly.

Fourth Embodiment

The above first to third embodiments describe cases in which information showing the status of the arm is displayed together with the graph generated by the graph generating unit 261. The fourth embodiment will describe a case in which information showing the status of a subject to be imaged is displayed. The fourth embodiment is different from the first to third embodiments in the contents displayed by the display controller 263. Hereinafter, this matter will be mainly described.

The display controller 263 according to the fourth embodiment allows, together with a graph, information showing the angle of a subject to be imaged when the arm is at an angle illustrated in the graph as information showing the status of the subject to be imaged. For example, the display controller 263 allows a three-dimensional image of a main artery with an angle at which the vertical cross section of the aortic valve is nearly perpendicular or horizontal to the display plane of an X-ray image, to be displayed as information showing the angle of a subject to be imaged.

Figure 15A:
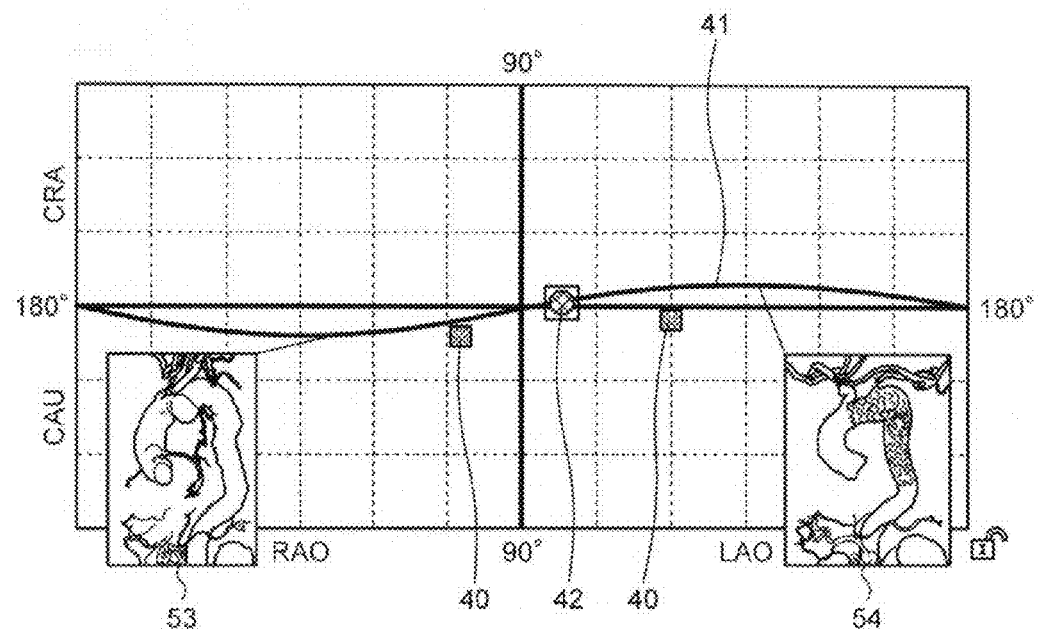
FIG. 15A is a diagram illustrating an example (1) of display control by a display controller according to a fourth embodiment.

FIG. 15A is a diagram illustrating an example (1) of display control by the display controller according to the fourth embodiment. For example, as illustrated in FIG. 15A, the display controller 263 according to the fourth embodiment allows the display unit 23 to display a display graph in which a three-dimensional image of a main artery (a 3D blood vessel image) with the C-arm angled at a particular angle is superimposed on a graph generated by the graph generating unit 261. As an example, as illustrated in FIG. 15A, the display controller 263 allows the display unit 23 to display a display graph in which a 3D blood vessel images 53 and 54 with the C-arm 15 angled at angles corresponding to the points on the curve 41, which is the optimal projection curve, are superimposed on a graph.

In other words, the display controller 263 allows the 3D blood vessel image generated by the image processor 26 to be superimposed on the graph generated by the graph generating unit 261 and to be displayed on the display unit 23. The 3D blood vessel image generated by the image processor 26 may be a projection image generated, when the C-arm 15 is angled at a designated angle, by reading the three-dimensional data of the subject out of the three-dimensional data collected by a medical image diagnostic apparatus such as an X-ray CT apparatus or an MRI apparatus and stored in advance for each subject, or may be a 3D blood vessel image read out of 3D blood vessel images, with the C-arm 15 angled at respective angles, stored in advance for each subject.

In one example, when an operator designates a point (angle) on the graph, the image processor 26 reads the three-dimensional data of a medical image with a subject ID as a key, and based on the read three-dimensional data, generates a 3D blood vessel image corresponding to the designated angle by projection processing. In other words, based on the body posture of a subject when the three-dimensional data is collected and the position of a viewpoint and the direction of a line of sight for performing projection on the three-dimensional data, the image processor 26 generates a 3D blood vessel image corresponding to the designated angle of the C-arm 15.

In another example, when the operator designates a point (angle), the image processor 26 reds a 3D blood vessel image corresponding to the designated angle with a subject ID as a key. The three-dimensional data collected by the medical image diagnostic apparatus and the 3D blood vessel images at respective angles are associated with the subject ID and stored in, for example, the image data storage unit 25.

Although FIG. 15A illustrates the 3D blood vessel image 53 and the 3D blood vessel image 54, this is a display example. A case of displaying one 3D blood vessel image is possible, and a case of displaying three or more 3D blood vessel images is also possible. In other words, the display controller 263 allows any 3D blood vessel image corresponding to a point within a graph designated by the operator to be optionally displayed.

For example, the display controller 263 allows a three-dimensional image of a main artery rotated by an angle at which the vertical cross section of the aortic valve is nearly perpendicular or horizontal to the display plane of an X-ray image, to be displayed as information showing the angle of a subject to be imaged.

Figure 15B:
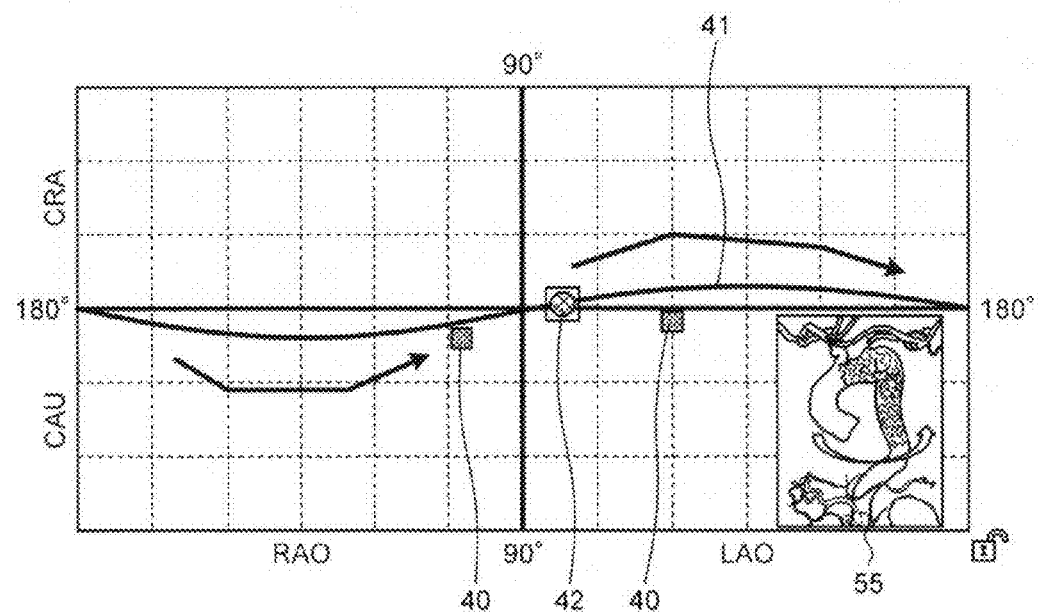
FIG. 15B is a diagram illustrating an example (2) of display control by the display controller according to the fourth embodiment.

FIG. 15B is a diagram illustrating an example (2) of display control by the display controller according to the fourth embodiment. For example, as illustrated in FIG. 15B, the display controller 263 according to the fourth embodiment allows the display unit 23 to display a display graph in which a 3D blood vessel image rotated by an angle at which the vertical cross section of the aortic valve is nearly perpendicular to the display plane of the X-ray image is superimposed on a graph generated by the graph generating unit 261. As an example, as illustrated in FIG. 15B, the display controller 263 allows the display unit 23 to display a display graph in which a 3D blood vessel images 55 when the angle of the arm is changed from left to right along the curve 41, which is the optimal projection curve, are superimposed on the graph.

In other words, the display controller 263 allows a moving image obtained by successively updating 3D blood vessel images corresponding to respective angles generated by the image processor 26 to be superimposed on the graph generated by the graph generating unit 261 and to be displayed on the display unit 23. The 3D blood vessel image generated by the image processor 26 may be a projection image for each angle generated, when the display of a moving image is designated, by reading the three-dimensional data of the subject out of three-dimensional data collected by a medical image diagnostic apparatus such as an X-ray CT apparatus or an MRI apparatus and stored in advance for each subject, or a 3D blood vessel image read out of a plurality of 3D blood vessel images of angles at which the vertical cross section of the aortic valve is nearly perpendicular to the display plane of an X-ray image and stored in advance for each subject.

In one example, when the operator selects the play button on the graph, the image processor 26 reads the three-dimensional data of a medical image with the subject ID as a key, and using the read three-dimensional data, generates a plurality of 3D blood vessel images corresponding to respective angles by projection processing. In another example, when the operator selects the regeneration button on the graph, the image processor 26 reads a plurality of 3D blood vessel images corresponding to respective angles with the subject ID as a key. The three-dimensional data collected by the medical image diagnostic apparatus and the 3D blood vessel images at respective angles are associated with the subject ID and stored in, for example, the image data storage unit 25.

Figure 16:
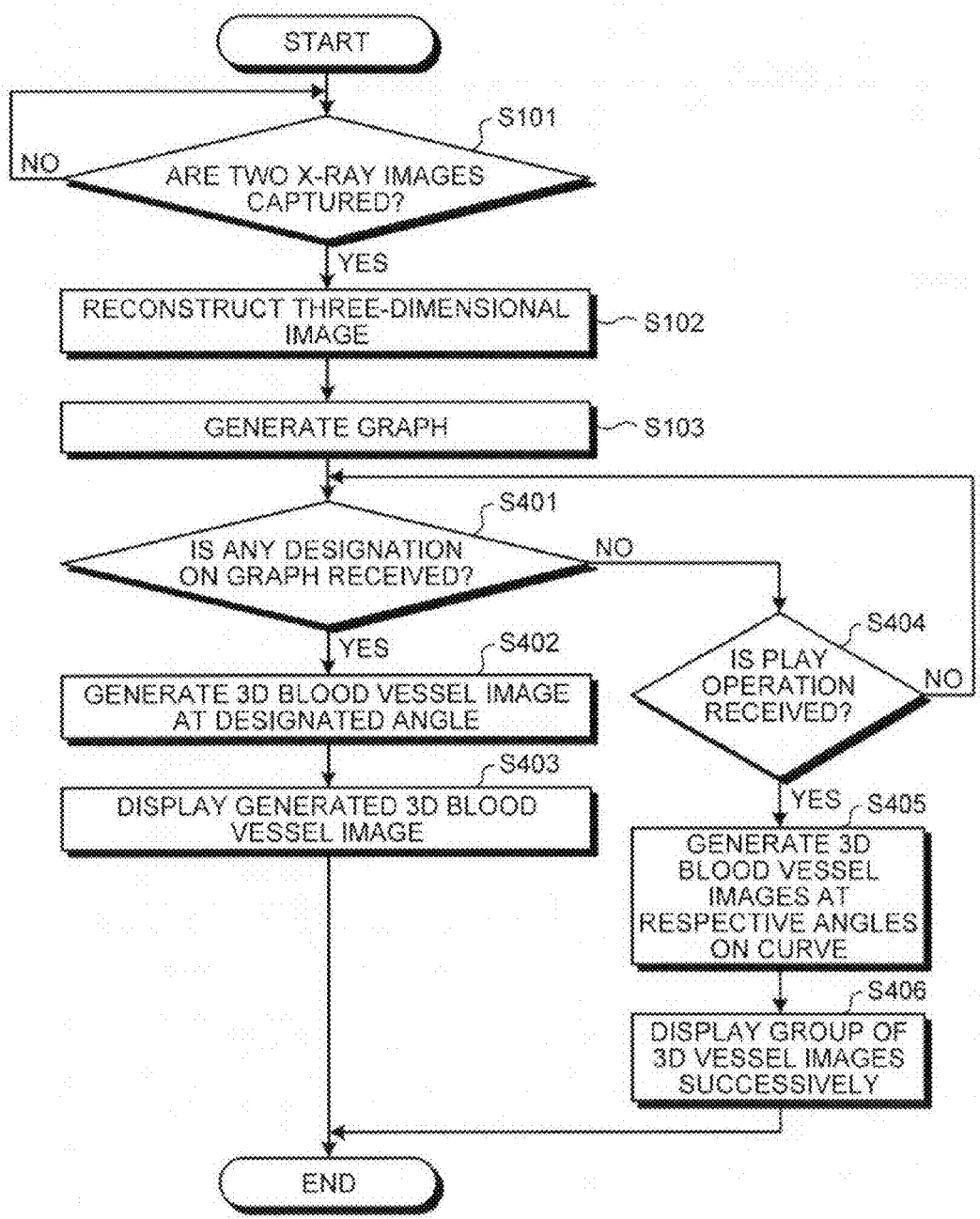
FIG. 16 is a flowchart illustrating the procedure of processing by an X-ray diagnostic apparatus according to the fourth embodiment.

Next, processing by the X-ray diagnostic apparatus 100 according to the fourth embodiment will be described using FIG. 16. FIG. 16 is a flowchart illustrating the procedure of the processing by the X-ray diagnostic apparatus 100 according to the fourth embodiment. In FIG. 16, like processing as in the procedure of the processing by the X-ray diagnostic apparatus 100 according to the first embodiment illustrated in FIG. 9 will be referred to by like step numbers, and the description of the details thereof will be omitted.

As illustrated in FIG. 16, in the X-ray diagnostic apparatus 100 according to the fourth embodiment, when two X-ray images for TAVR are captured (Yes at S101), the graph generating unit 261 reconstructs a three-dimensional image (S102) and generates a graph (S103). The image processor 26 then determines whether designation on the graph is received (S401).

When designation on the graph is received (Yes at S401), the image processor 26 generates a 3D blood vessel image at the designated angle (S402). The display controller 263 allows the display unit 23 to display a display graph in which the generated 3D blood vessel image is superimposed on the graph (S403).

When no designation on the graph is received (No at S401), the image processor 26 determines whether a play operation is received (S404). When the play operation is received (Yes at S404), the image processor 26 generates 3D blood vessel images at respective angles on the curve (S405). The display controller 263 allows the display unit 23 to display a display graph in which the group of 3D blood vessel images played are successively displayed and are superimposed on the graph (S406).

Until the two X-ray images are captured, the X-ray diagnostic apparatus 100 is on standby (No at S101). The X-ray diagnostic apparatus 100 is on standby until designation on the graph is received (No at S401), or the X-ray diagnostic apparatus 100 is on standby until the play operation is received (NO at S404).

As described above, in the fourth embodiment, the display controller 263 allows a three-dimensional image of a main artery with an angle at which the vertical cross section of the aortic valve is nearly perpendicular or horizontal to the display plane of an X-ray image, to be displayed as information showing the angle of the subject to be imaged. The X-ray diagnostic apparatus 100 according to the fourth embodiment thus displays in advance the appearance of the main artery when the C-arm 15 is angled. For example, this allows the state of calcification, the appearance of coronary arteries, the appearance of the valve, or the like to be checked in advance. As a result, the X-ray diagnostic apparatus 100 according to the fourth embodiment allows the optimal angle to be checked before operation.

For example, the coronary arteries are present a few centimeters above the aortic valve to supply the heart with nutrition and oxygen. In TAVR, thus, it is extremely important not to block the coronary arteries with the artificial valve. Given this situation, using the X-ray diagnostic apparatus 100 according to the fourth embodiment allows the aortic valve to be observed in the vertical direction and allows the angle of the arm that provides proper observation of the state of the coronary arteries or the like to be checked before its operation.

In the fourth embodiment, the display controller allows the a three-dimensional image of a main artery rotated by an angle at which the vertical cross section of the aortic valve is nearly perpendicular or horizontal to the display plane of an X-ray image, to be displayed as information showing the angle of a subject to be imaged. The X-ray diagnostic apparatus 100 according to the fourth embodiment thus displays in advance the appearance of the main artery when the main artery is viewed in the vertical direction.

Fifth Embodiment

The above first to fourth embodiments describe cases in which the optimal projection curve is generated from two X-ray images. The fifth embodiment will describe a case in which the optimal projection curve is generated from, in addition to the two X-ray images, a three-dimensional image such as a CT image. The fifth embodiment is different from the first to fourth embodiments in the processing contents by the graph generating unit 261 and the display controller 263. Hereinafter, these matters will be mainly described.

Based on two X-ray images captured in two directions and a three-dimensional medical image, the graph generating unit 261 according to the fifth embodiment generates respective diagrams illustrating the angle information of the arm with which the vertical cross section of the aortic valve is displayed at an angle nearly perpendicular or horizontal to the display plane of an X-ray image. For example, as described above, the graph generating unit 261 generates the optimal projection curve using the two X-ray images captured in the two directions.

The graph generating unit 261 collects designated angles of the C-arm 15 based on the physical posture of the subject when the three-dimensional data is collected and the position of a viewpoint and the direction of a line of sight for performing projection on the three-dimensional data. As an example, the graph generating unit 261 calculates the angle of the C-arm 15 based on the physical posture of the subject and the position of a viewpoint and the direction of a line of sight allowing the aortic valve to be observed in the vertical direction.

Figure 17:
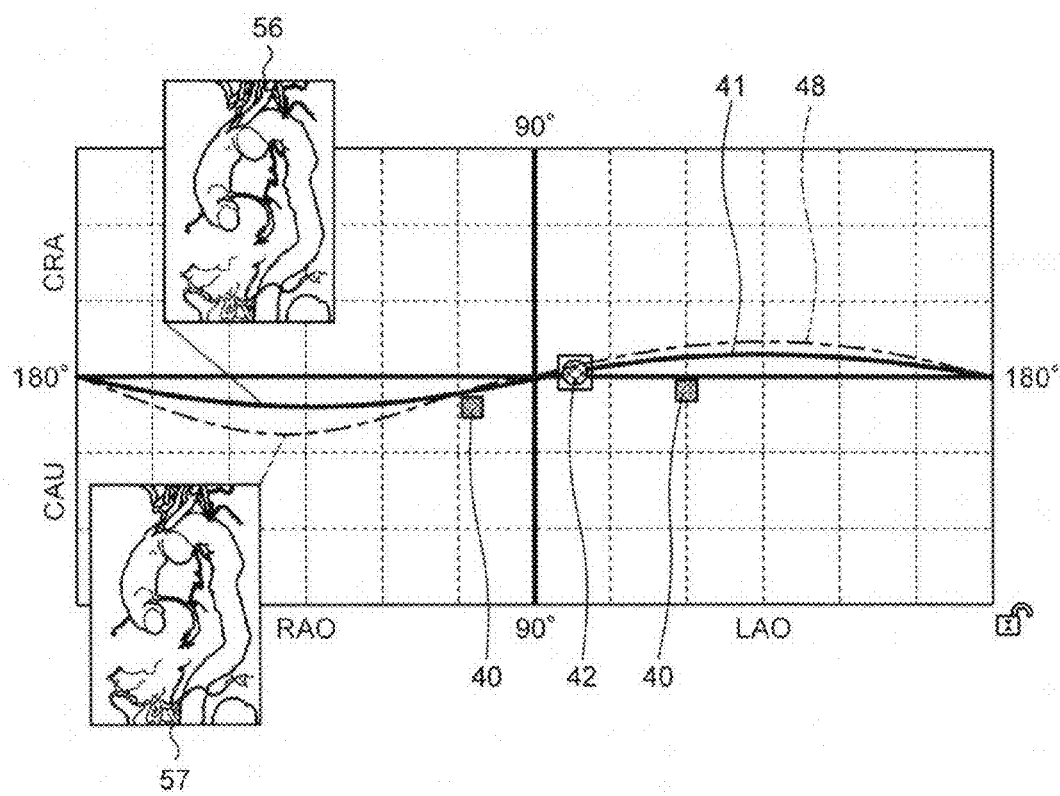
FIG. 17 is a diagram illustrating an example of display control by a display controller according to a fifth embodiment.

When there is a difference between the angle information of the arm based on the two X-ray images and the angle information of the arm based on the three-dimensional medical image, the display controller 263 according to the fifth embodiment allows three-dimensional images of the main artery corresponding to both pieces of angle information, to be displayed. FIG. 17 is a diagram illustrating an example of display control by the display controller according to the fifth embodiment.

For example, as illustrated in FIG. 17, the display controller 263 according to the fifth embodiment allows three-dimensional blood vessel images at a position having a large difference between the curve 41 based on the two X-ray images generated by the graph generating unit 261 and a curve 48 based on the three-dimensional CT image, to be displayed. As an example, as illustrated in FIG. 17, the display controller 263 allows the display unit 23 to display a display graph in which a 3D blood vessel image 56 corresponding to the curve 41 that is the optimal projection curve, based on the two X-ray images and a 3D blood vessel image 57 corresponding to the curve 48 that is the optimal projection curve based on the CT image are superimposed on the graph. For the generation of the 3D blood vessel images, the same method as described above is used.

The X-ray diagnostic apparatus 100 according to the fifth embodiment thereby allows understanding in which part of an image a difference arises due to a difference in the angle of the C-arm 15.

Figure 18:
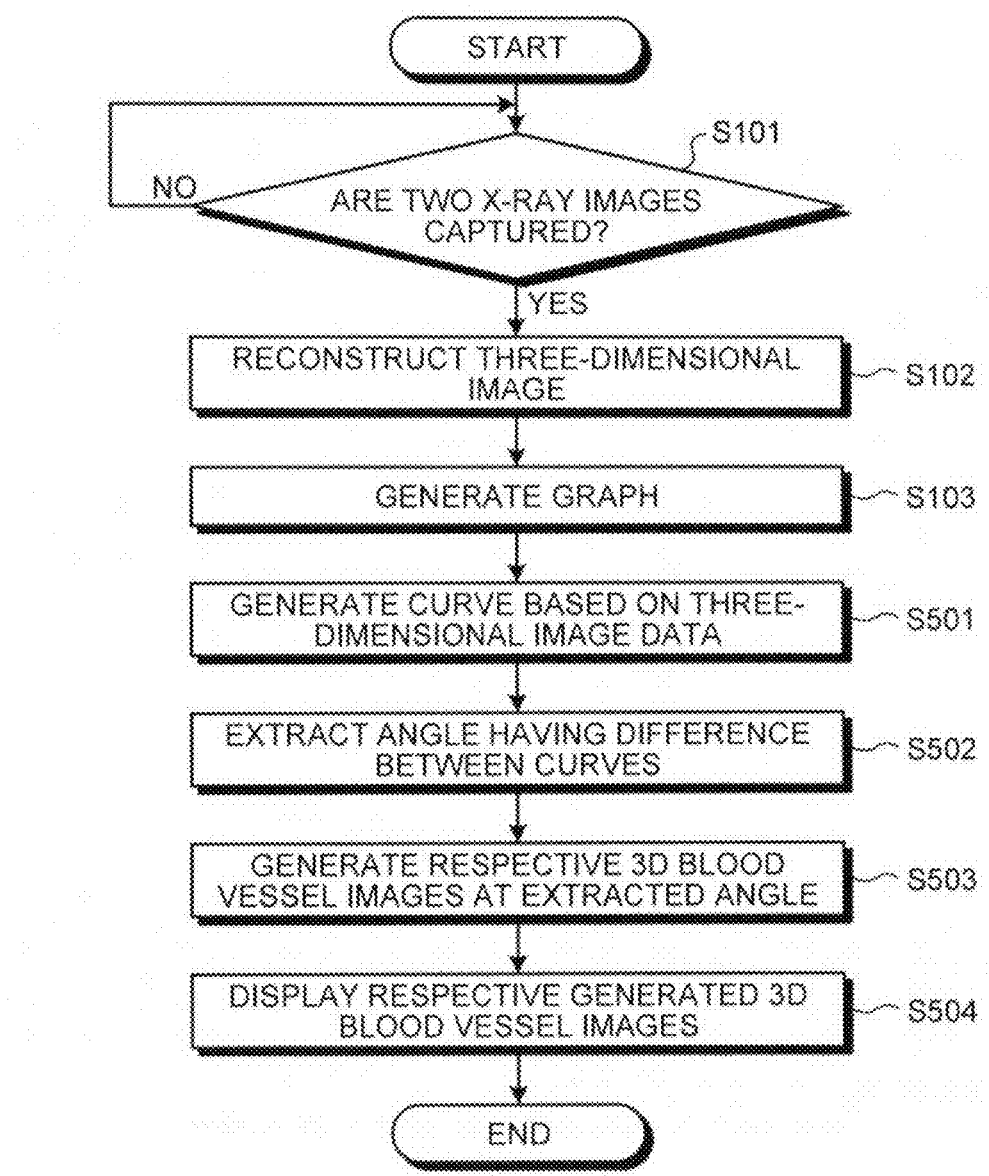
FIG. 18 is a flowchart illustrating the procedure of processing by an X-ray diagnostic apparatus according to the fifth embodiment.

Next, processing by the X-ray diagnostic apparatus 100 according to the fifth embodiment will be described using FIG. 18. FIG. 18 is a flowchart illustrating the procedure of the processing by the X-ray diagnostic apparatus 100 according to the fifth embodiment. In FIG. 16, like processing as in the procedure of the processing by the X-ray diagnostic apparatus 100 according to the first embodiment illustrated in FIG. 9 will be referred to by like step numbers, and the description of the details thereof will be omitted.

As illustrated in FIG. 18, in the X-ray diagnostic apparatus 100 according to the fifth embodiment, when two X-ray images for TAVR are captured (Yes at S101), the graph generating unit 261 reconstructs a three-dimensional image (S102) and generates a graph (curve) (S103). The image processor 26 then generates a curve based on the three-dimensional image data (S501).

The display controller 263 then extracts an angle having a difference between the generated curves (S502). After that, the image processor 26 generates respective 3D blood vessel images at the extracted angle (S503). The display controller 263 then allows the display unit 23 to display a display graph in which the generated 3D blood vessel images are superimposed on the graph (S504). FIG. 18 describes a case in which, after the curve based on the two X-ray images is generated, the curve based on the three-dimensional image is generated. The embodiment is not limited thereto. For example, a case in which they are generated at the same time is possible, and a case in which, after the curve based on the three-dimensional image is generated, the curve based on the two X-ray images is generated is also possible.

As described above, in the fifth embodiment, based on two X-ray images captured in the two directions and a three-dimensional medical image, the graph generating unit 261 generates respective images illustrating the angle information of the arm with which the vertical cross section of the aortic valve is displayed at an angle nearly perpendicular or horizontal to the display plane of the X-ray image. When there is a difference between the angle information of the arm based on the two X-ray images and the angle information of the arm based on the three-dimensional medical image, the display controller 263 allows three-dimensional images of the main artery corresponding to both pieces of angle information to be displayed. The X-ray diagnostic apparatus 100 according to the fifth embodiment thus generates a graph based on different pieces of data, thereby allowing a difference between the pieces of data to be checked. The X-ray diagnostic apparatus 100 according to the fifth embodiment allows, for example, the 3D blood vessel images based on both curves to be referred to, thereby allowing a graph with higher precision to be selected and used.

Sixth Embodiment

The first to fifth embodiments have been so far described. Various different embodiments other than the above first to fifth embodiments may be performed.

Although the above first to fifth embodiments describe a case in which the motion area, the non-motion area, and the interference area of the arm are illustrated on the graph, a case in which a 3D model representing the apparatus, the subject, the couch, the peripheral equipment, the operator, or the like is illustrated on the graph, and a case in which a 3D blood vessel image is illustrated on the graph, an embodiment is not limited thereto and may be a combination thereof as appropriate.

Figure 19:
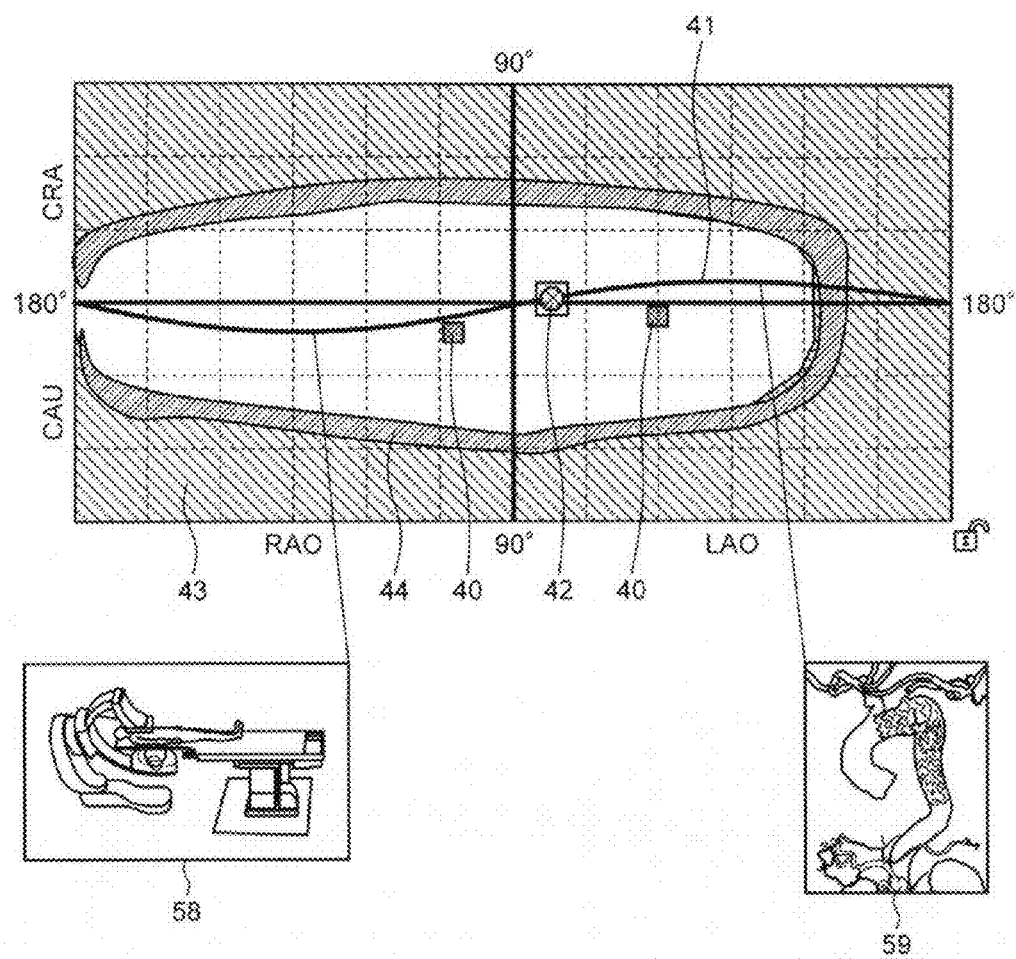
FIG. 19 is a diagram illustrating an example of display control by a display controller according to a sixth embodiment.

FIG. 19 is a diagram illustrating an example of display control by the display controller 263 according to the sixth embodiment. For example, as illustrated in FIG. 19, the display controller 263 according to the sixth embodiment allows the display unit 23 to display a display graph in which the non-motion area of the C-arm 15 calculated by the calculating unit 262 is superimposed on the graph generated by the graph generating unit 261. Furthermore, the display controller 263 allows a 3D model 58, a 3D blood vessel image 59, or the like at an angle on the curve 41 to be superimposed and to be displayed on the display unit 23. The example illustrated in FIG. 19 is an example, and an embodiment is not limited thereto. In other words, information displayed by the display controller 263 may be changed optionally. For example, the non-motion area and the 3D model may be displayed on the graph, or the non-motion area and the 3D blood vessel image may be displayed on the graph.

The information displayed on the graph may be an X-ray image. For example, the display controller 263 allows an X-ray image at the current position of the C-arm 15 to be superimposed and displayed on the graph. For example, fluoroscopic images captured when the optimal projection curve is generated may be stored in a memory and displayed. As an example, when a point (angle) on the graph is designated, the display controller 263 allows the display unit 23 to display a particular number of images starting with a fluoroscopic image that is the closest to the designated angle out of the stored fluoroscopic images as thumbnail images. When a selection operation for a displayed thumbnail image is received, the display controller 263 displays a fluoroscopic image corresponding to the selected thumbnail image in a large size.

The above example is an example, and an embodiment is not limited thereto. In other words, the X-ray image to be displayed is not limited to the fluoroscopic image, and may be, for example, a captured image.

The above first to fifth embodiments describe cases in which the angle of the C-arm is determined. However, an embodiment is not limited thereto. For example, the angle of an Ω arm may be determined.

The above first to fifth embodiments describe cases in which, as the non-motion area of the C-arm 15, a non-motion area due to the stroke limits of the arm and an interference area are calculated to be displayed on the graph. However, an embodiment is not limited thereto. For example, either of them may be calculated to be displayed.

The above first to fifth embodiments describe cases in which the clinical analysis application "cardiovascular angiographic analysis system aortic valve (CAAS A-Valve) by Pie Medical Imaging, LLC." is used for the generation of the graph. However, an embodiment is not limited thereto. For example, any means that displays the angle information of an arm on a clinical angle graph may be applicable.

The above second embodiment describes a case in which the C-arm 15 is moved to the angle of the arm after the input operation on the graph displayed on the display unit 23 has been finished. However, an embodiment is not limited thereto. For example, the arm may move simultaneously following operation on the graph.

In such a case, the input unit 22 successively informs the system controller 21 of angle information while dragging with a mouse is performed during input operation, and the system controller 21 informs the C-arm/couchtop mechanism controller 19 of the informed angle information, thereby allowing the arm to be moved simultaneously following the movement of the mouse during input operation.

As described above, in the first to sixth embodiments, the X-ray apparatus improves operability associated with setting the angle of the arm.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
a generating unit configured to generate a diagram illustrating angle information of an arm of the X-ray diagnostic apparatus;
a display controller configured to perform display control to visualize, together with the diagram generated by the generating unit, at least one of information showing the status of the arm when the arm is at an angle illustrated in the diagram and information showing the status of a subject to be imaged when the arm is at the angle illustrated in the diagram; and
a calculating unit configured to calculate an interference area between the arm and a subject or a couch as information showing the status of the arm based on the current position information of the arm, wherein
the generating unit generates a graph as information showing the angle information, and
the display controller allows, together with the graph, at least any one of the motion area of the arm, an area beyond the motion limit of the arm, and the interference area to be displayed as information showing the status of the arm.

2. The X-ray diagnostic apparatus according to claim 1, wherein
the generating unit generates a graph as information showing the angle information, and
the display controller allows, together with the graph, an outside view illustrating the position relation between the arm and a subject or a couch to be displayed as information showing the status of the arm.

3. The X-ray diagnostic apparatus according to claim 2, wherein the display controller allows a position relation with at least one of peripheral equipment and an operator to be further displayed on the outside view as information showing the status of the arm.

4. The X-ray diagnostic apparatus according to claim 1, wherein
the generating unit generates a graph as information showing the angle information, and
the display controller allows, together with the graph, information showing the angle of the subject to be imaged when the arm is at an angle illustrated in the graph to be displayed as information showing the status of the subject to be imaged.

5. The X-ray diagnostic apparatus according to claim 4, wherein the display controller allows a three-dimensional image of a main artery with an angle at which a vertical cross section of an aortic valve is nearly perpendicular or horizontal to the display plane of an X-ray image to be displayed as information showing the angle of the subject to be imaged.

6. The X-ray diagnostic apparatus according to claim 4, wherein the display controller allows a three-dimensional image of a main artery rotated by an angle at which a vertical cross section of an aortic valve is nearly perpendicular or horizontal to the display plane of an X-ray image to be displayed as information showing the angle of the subject to be imaged.

7. The X-ray diagnostic apparatus according to claim 4, wherein
based on two X-ray images captured in two directions and a three-dimensional medical image, the generating unit generates respective diagrams illustrating the angle information of the arm with which a vertical cross section of an aortic valve is displayed with an angle nearly perpendicular or horizontal to the display plane of an X-ray image, and
when there is any difference between the angle information of the arm based on the two X-ray images and the angle information of the arm based on the three-dimensional medical image, the display controller allows three-dimensional images of a main artery corresponding to both pieces of angle information to be displayed.

8. The X-ray diagnostic apparatus according to claim 1, wherein the generating unit generates a graph illustrating the angle information of the arm at which a vertical cross section of an aortic valve is nearly perpendicular or horizontal to the display plane of an X-ray image.

9. The X-ray diagnostic apparatus according to claim 8, wherein the vertical cross section is a plane that is nearly perpendicular to the aortic valve when the aortic valve is closed.

10. The X-ray diagnostic apparatus according to claim 1, wherein the display controller allows the current position of the arm and a position whose distance from the current position of the arm is shortest out of the angles of the arm at which an aortic valve is displayed with a predetermined angle with respect to the display plane of an X-ray image to be further displayed on the diagram.

11. The X-ray diagnostic apparatus according to claim 1, further comprising:
an input unit configured to receive an input operation onto a diagram displayed by a predetermined display unit, and
an arm controller configured to move the arm in accordance with the input operation received by the input unit.

* * * * *